US 7,005,537 B2

(12) United States Patent
Mozeleski et al.

(10) Patent No.: US 7,005,537 B2
(45) Date of Patent: Feb. 28, 2006

(54) PRODUCTION OF ESTERS (75) Inventors: Edmund J. Mozeleski, Califon, NJ (US); Carl R. Beck, Greenwell Springs, LA (US); Kirk C. Nadler, Houston, TX (US); Richard H. Schlosberg, Bridgewater, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 719 days.

(21) Appl. No.: 09/750,567

(22) Filed: Dec. 26, 2000

(65) Prior Publication Data

US 2001/0041808 A1 Nov. 15, 2001

Related U.S. Application Data (60) Provisional application No. 60/173,504, filed on Dec. 29, 1999.

(51) Int. Cl.
*C07C 67/36* (2006.01)
*C07C 67/38* (2006.01)
*C07C 67/24* (2006.01)

(52) U.S. Cl. .................. 560/233; 560/232; 560/240
(58) Field of Classification Search .............. 560/233, 560/322, 240, 232
See application file for complete search history.

(56) References Cited

U.S. PATENT DOCUMENTS

| | | | |
|---|---|---|---|
| 2,967,873 A | 1/1961 | Koch et al. | 260/410.9 |
| 4,311,851 A | * 1/1982 | Jung et al. | 560/233 |
| 4,894,188 A | * 1/1990 | Takahashi et al. | 554/130 |
| 5,552,080 A | 9/1996 | Bolmer | 510/412 |

FOREIGN PATENT DOCUMENTS

| | | |
|---|---|---|
| GB | 1 232 317 | 5/1971 |
| WO | 0 017 441 A1 | 10/1980 |
| WO | PCT/US99/09885 | 5/1999 |

OTHER PUBLICATIONS

J. Falbe, "New Synthesis with Carbon Monoxide," Springer–Verlag, Sec. 5.7, pp. 406–413, 1980.
40 C.F.R. 80.27, "Controls and Prohibitions on Gasoline Volatility."
Carter, W.P.L., "Preliminary Report to California Air Resources Board under Contract No. 95–308," Aug. 6, 1998.
"Toxicology," *Kirk–Othmer Encyclopedia of Chemical Technology*, 4th Ed., vol. 24, pp. 456–490.
"Table 2: Physical Properties of Common Industrial Solvents," *Kirk–Othmer Encyclopedia of Chemical Technology*, 4th Ed., vol. 22, pp. 536–548.
Dante et al., "Program Calculates Solvent Properties and Solubility Parameters," *Modern Paint and Coatings*, Sep., 1989.

* cited by examiner

*Primary Examiner*—Cecilia J. Tsang
*Assistant Examiner*—Taylor Victor Oh (57) ABSTRACT Disclosed is a process for the production of esters. In particular, the process includes contacting an olefin or an ether with carbon monoxide and an acid composition comprising $BF_3 \cdot 2CH_3OH$ to from a product composition, adding an alcohol to the product composition, and separating the $BF_3 \cdot 2CH_3OH$ from the ester. The separated $BF_3 \cdot 2CH_3OH$ may then be recycled to the reaction unit.

52 Claims, 1 Drawing Sheet

Fig. 1

PRODUCTION OF ESTERS

CROSS REFERENCE

This application claims priority to U.S. Provisional Application Ser. No. 60/173,504 filed Dec. 29, 1999, which is incorporated herein in its entirety.

FIELD OF THE INVENTION

This invention relates to a process for the production of esters from olefins and ethers.

BACKGROUND OF THE INVENTION

Esters are compounds which currently find use in such areas as pesticides and herbicides, metal extraction agents, synthetic lubricants, polymerization aids for acrylic acid esters, insect attractants and repellants, industrial fragrances, odorants and cosmetic components, pharmaceutical applications, and photographic applications. Esters are typically made from a two step process. First, the corresponding carboxylic acid is produced. The acid is then reacted with an alcohol to produce the desired ester via a condensation process.

High volume production of dialkyl esters (two alkyl groups at the α-carbon) and trialkyl esters (three alkyl groups at the α-carbon) can be very difficult to prepare from the corresponding acid because of the hydrolytic instability of the product esters. Koch and Moller (U.S. Pat. No. 2,967,873) describe a synthesis of trialkyl esters from olefins using a catalyst system of $BF_3.H_2O.ROH$ where ROH is an aliphatic alcohol of low molecular weight and an olefin having six or more carbons. However, this process always produces some carboxylic acid along with the desired ester and requires continual adjustment of the water to alcohol ratio in the recycled $BF_3$ catalyst.

Commercial use of this technology is currently employed by Exxon Chemical Company (Baton Rouge, La.) and Shell (Pernes, Holland). ExxonMobil's products are known as "neo acids" while Shell's products are called Versatic™ acids. ExxonMobil Chemical employs $BF_3.2H_2O$ as catalyst and Shell employs $H_3PO_4.BF_3.H_2O$ in a 1:1:1 ratio (J. Falbe, "New Synthesis with Carbon Monoxide", Springer-Verlag, 1980, p. 406). Olefins used in these processes include isobutylene, propylene oligomers and $C_8$–$C_{11}$ fractions. The major commercial products are 1,1,1-trimethyl acetic acid (pivalic acid or neopentanoic acid) and neodecanoic acid or Versatic™10. The major disadvantage of these processes is the difficulty, relatively high cost, and process inefficiencies in recycling the acid catalyst in the process.

Gelbein (Re. 31,010) discloses a one step process for the preparation of esters from olefins in the presence of $BF_3.CH_3OH$. This process requires that uncomplexed $BF_3$ be distilled from the reaction products. This distillation is very inefficient and requires the use of corrosion resistant processing equipment. Following the distillation of uncomplexed $BF_3$, methanol is added to form an azeotrope with the desired ester and a $BF_3.2CH_3OH$ adduct. The distilled $BF_3$ or fresh $BF_3$ is added to $BF_3.2CH_3OH$ to form $BF_3.CH_3OH$, which is recycled to the reaction unit. The $BF_3.CH_3OH$ is a preferred because it is stronger acid than $BF_3.2CH_3OH$, and the esterfication of propylene or ethylene can occur at temperatures below 100° C., preferably below 60° C.

Jung and Peress (U.S. Pat. No. 4,311,851) also disclose the preparation of esters from a $BF_3.ROH$ complex catalyst. This process also requires that uncomplexed $BF_3$ be distilled from the reaction products and then recycled to form the active $BF_3.ROH$ catalyst.

Large volume, commercial scale production of dialkyl and trialkyl esters remains a problem in the chemical industry. Presently, the production of these esters, particularly trialkyl esters (neo acid esters), are limited by having to use a relatively large amount of purified acid catalyst and/or by having to distill off a corrosive strong acid (HF or $BF_3$) from the reaction products so the acid can be recycled in the process. Distillation of this acid requires special operational handling and specialized process units which results in a highly inefficient process.

BRIEF SUMMARY OF THE INVENTION

The invention provides a selective process to dialkyl and trialkyl esters from olefins and ethers. The invention provides a method to recover and recycle the acid catalyst without the need to distill $BF_3$ from the reaction products. The process comprises contacting an olefin or ether with carbon monoxide and an acid composition containing $BF_3.2ROH$ to form a product composition, adding ROH to the product composition, and separating an acid product comprising $BF_3.2ROH$ from the ester. The acid composition will have a molar ratio of ROH:$BF_3$ from about 1.6:1 to about 3:1, preferably from about 1.9:1 to about 3:1. The process may further include recycling a portion of the separated acid product to contact the olefin or ether. It may also be desirable to contact the olefin or ether with phosphoric acid.

The separation of the acid product from the product esters may take place in multiple separation units. The separation process may include concentrating the acid product such that the molar ratio ROH:$BF_3$ of the concentrated acid product is from about 2:1 to about 4:1, preferably from about 2:1 to about 3:1.

The separation of the acid product from the product esters may be facilitated by the presence of a hydrocarbon, wherein the hydrocarbon is selected from a saturated linear or branched hydrocarbon having at least six carbons. The hydrocarbon can be added to the reaction unit as a co-solvent in the carbonylation reaction, and/or one or more separation units as an extracting solvent.

The carbonylation reaction in the process includes contacting the olefin or ether with the carbon monoxide and acid composition at a temperature from about 60° C. to about 200° C., preferably from about 110° C. to about 160° C. The pressure of the carbonylation reaction includes contacting the olefin or ether at a pressure from about 30 atm to about 200 atm, preferably from about 110 atm to about 160 atm.

BRIEF DESCRIPTION OF THE DRAWINGS

This invention will be better understood by reference to the Detailed Description of the Invention when taken together with the attached drawings, wherein.

DETAILED DESCRIPTION OF THE INVENTION

In this invention, a variety of dialkyl and trialkyl acid esters are produced from olefin or ether feedstocks, carbon monoxide, and an acid composition containing $BF_3.2ROH$, wherein ROH is an alcohol and $BF_3$ is boron trifluoride. The olefin feedstock may be obtained from a variety of sources, including a dilute olefin feedstock from the steam cracking of hydrocarbons. The carbon monoxide (CO) can be used in a relatively pure form, or the CO can be mixed with an inert gas, e.g., hydrogen, nitrogen, carbon dioxide, or mixtures thereof. If a gas mixture is used, the CO concentration should be at least about 40% by volume. Preferably, the CO concentration in the gas mixture is at least about 90% by volume. The alcohol is selected from methanol, n-propanol, n-butanol, 2-propanol, 2-ethyl hexanol, isohexanol, isoheptanol, isooctanol, isononanol, 3,5,5-trimethyl hexanol, isodecanol, isotridecanol, 1-octanol, 1-decanol, 1-dodecanol, 1-tetradecanol and the mixtures thereof. Preferably, the alcohol is methanol. If MTBE is used as the feed ether, methanol is preferably used as the alcohol.

In contrast to prior olefin carbonylations, the molar concentration of the alcohol should be greater than the molar concentration of the $BF_3$ in the acid composition. Typically, the molar concentration of alcohol to the molar concentration of $BF_3$ is from about 1.6:1 to about 4:1, preferably from about 1.9:1 to about 3:1, most preferably from about 2:1 to about 2.5:1. Because the acid composition contains primarily $BF_3.2ROH$, rather than $BF_3.ROH$, the invention utilizes a relatively weaker acid to convert olefin or ethers to the desired ester products. The strength of the acid depends upon the relative molar concentration ratio of alcohol:$BF_3$. The greater the molar concentration ratio the weaker the acid.

After the olefin or ether contacts the CO and the acid composition for the desired amount of time, the product composition is cooled and the excess CO vented. An alcohol is added to the product composition to quench the reaction. Preferably, the alcohol used is the same alcohol that is contained in the acid composition. The addition of the alcohol results in the formation of an azeotrope containing the desired ester products and alcohol, and an acid product. The acid product contains $BF_3.2ROH$, as well as the azeotrope, which contains alcohol and the product esters.

The azeotrope and the acid product are then separated. Complete or near complete separation of the azeotrope from the acid product may require one or more separation steps. The desired product esters are distilled from the azeotrope to give the alcohol and any remaining acid product that may remain after the separation. The alcohol can be recycled to the reactor, to one or more separation units, or to any combination thereof. A portion of the separated acid product, preferably with little or no purification step, is recycled to the reactor. Distillation of $BF_3$ from the product composition or the acid product is not carried out in the process. Instead, the acid product is concentrated by removal of alcohol and the remaining azeotrope that may remain in the acid product following one or more separations.

In the preferred embodiment, the acid product is concentrated by removing the alcohol and azeotrope under vacuum at elevated temperatures. The pressure during the acid concentration process is from about 0.01 mmHg to 200 mmHg, preferably from 0.1 mmHg to 100 mmHg, most preferably from 1 mmHg to 50 mmHg. The temperature during the acid concentration process is from about 30° C. to about 110° C., preferably from about 50° C. to about 90° C.

The concentrated acid product, which comprises primarily $BF_3.2ROH$, is recycled to the reactor. In some cases an acid purge stream is used to control and maintain the quality of the acid catalyst in the process. The molar ratio of alcohol:$BF_3$ in the concentrated acid product is from about 2 to 5, preferably from about 2 to 3, most preferably, the molar ratio of alcohol:$BF_3$ is about 2 before the acid product is recycled to the reactor.

In the carbonylation reaction, which is catalyzed by the acid composition, the respective molar concentrations of the acid and the alcohol should be greater than the molar concentration of the olefin or ether in the reaction mixture. Typically, the molar concentration of the alcohol to the molar concentration of the olefin or ether is from about 2:1 to about 20:1, preferably from about 2:1 to about 10:1, most preferably from about 2:1 to about 6:1. Typically, the molar concentration of $BF_3$ to the molar concentration of the olefin or ether is from about 0.5:1 to about 15:1, preferably from about 1:1 to about 8:1, most preferably from about 1:1 to about 6:1.

In the process of the invention, the olefin or ether is carbonylated in the presence of the acid catalyst at an effective carbonylation temperature and pressure, which minimizes undesirable side reactions to oligomers and other products. The catalytic reaction of olefin or ethers to dialkyl and trialkyl esters may be performed at temperatures from about 30° C. to about 200° C., preferably from about 110° C. to about 170° C., more preferably from about 120° C. to about 150° C. The specific temperature requirement is a function of the olefin or ether used in the process as well as the reaction pressure.

To minimize undesirable side reactions (typically olefin oligomerization reactions) it is desirable to maintain a large excess of CO in the reaction. This ratio is controlled by a number of parameters including: the reaction pressure, the rate of olefin feed, and the extent and effectiveness of mixing of the reactants and catalyst in the reaction vessel. The reaction pressure is not critical so long as a stochiometric excess of carbon monoxide is maintained in the reactor. The total pressure in the reactor is from about 30 atm to 200 atm, preferably from about 70 atm to about 160 atm, more preferably from about 110 atm to about 160 atm. These pressures are within current commercial unit capabilities for such carbon monoxide containing processes as hydroformylation and neoacid production.

In a batch process a large excess of the carbon monoxide is available to react with the olefin. In a continuous process the reaction process begins with an excess of acid catalyst, alcohol, and CO, however, once steady state conditions are achieved, the feed rate of CO can be maintained such that about one mole of CO is fed to the reactor for every mole of olefin or ether fed to the reactor.

Following the addition of the alcohol a phase separation between the acid product and the azeotrope may not occur. This phase separation will depend upon the olefin or ether as well as the alcohol used in the process. Generally, the greater number of carbons in the olefin, ether, and/or alcohol the greater likelihood of a phase separation.

Separation of the azeotrope and the acid product can be facilitated by the addition of a hydrocarbon. The hydrocarbon can be added to a separation unit as an extracting solvent, or added to the reactor as a co-solvent in the carbonylation reaction. In certain instances it may be desirable to add the hydrocarbon to the separation unit as well as the reactor. The hydrocarbon is a saturated, linear and/or branched hydrocarbon having at least six carbons. Preferably, the hydrocarbon is selected from the hexanes, heptanes, octanes, nonanes, or any combination thereof.

The separation units that may be used in the invention are known to those of ordinary skill in the art. Such separation units include a liquid-liquid extraction unit including a counter-flow extraction unit with mixing wells or plates.

Following the separation of the azetrope containing the ester products from the acid product, the ester products are separated from the azeotrope, hydrocarbon and alcohol. This separation can be carried out in a distillation column under conditions required to obtain the desired product specifications. The hydrocarbon or alcohol from the distillation can be recycled to the reactor or one or more separation units.

In one embodiment, phosphoric acid may be used as a co-catalyst in the reaction without adversely effecting product separation, catalyst recovery, and reaction selectivity. In some instances the addition of about 0.25 mol of $H_3PO_4$ per mole of $BF_3$ may result in a small improvement in product selectivity and/or product yield of the desired ester product.

Figure 1:
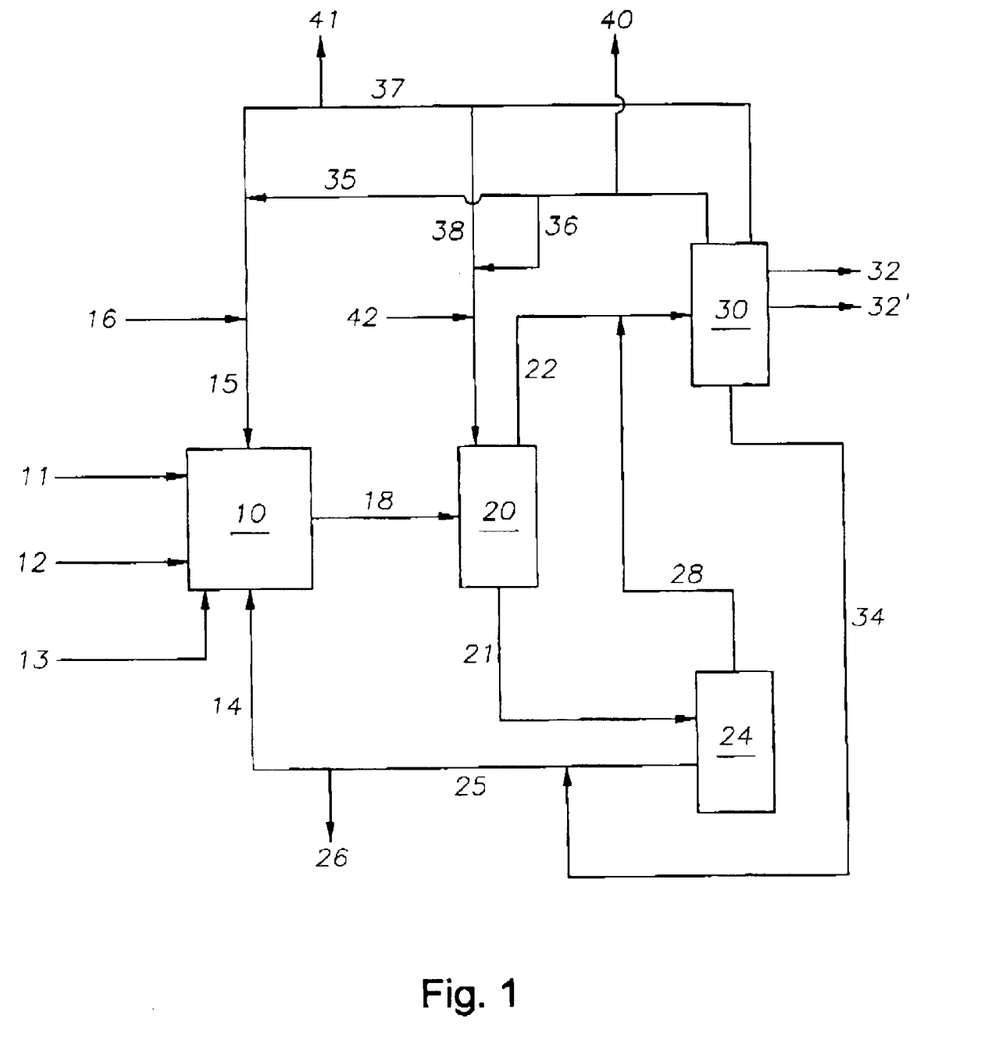
FIG. 1 is a schematic diagram of one embodiment of the invention.

FIG. 1 describes one embodiment of the invention. Fresh feed streams into the reactor 10 include CO 11, olefin or ether, 12, and $BF_3$ 13. An acid recycle stream 14 and an alcohol/hydrocarbon recycle stream 15 is also directed to the reactor 10. Fresh alcohol 16 can be added to the process in any number of ways, including to the reactor 10, the separation unit 20, or the alcohol/hydrocarbon recycle stream 15. A portion of the reaction product 18 is directed to a separation unit 20. Alcohol is added to the reaction product 18 in the separation unit 20. A portion of the acid product 21 is separated from the product containing the esters 22 in separation unit 20. In most embodiments additional separation units are required to maximize the separation of the acid product from the product containing the esters. As a result, the acid product 21 from separation unit 20 is directed to separation unit 24. The concentrated acid product 25 from the separation unit 24 is directed to the reactor 10. In many instances an acid purge stream 26 is required to maintain and control the quality of the acid catalyst in the reactor 10. Additional ester and alcohol is recovered from separation unit 24.

Stream 28 is combined with product stream 22 which is directed to a separation unit 30. Preferably, separation unit 30 contains one or more distillation columns to separate the desired ester products from the alcohol, any remaining acid product, and hydrocarbon. The desired ester products exit the separation zone 30 as ester product streams 32 and 32'. Acid product 34 from separation unit 30 is directed to concentrated acid product stream 25. A portion of the alcohol from separation unit 30 may be directed to the reactor via stream 35 or directed to separation unit 20 via stream 36. Because the concentrated acid product 25 is primarily $BF_3 \cdot 2ROH$, that is, the alcohol:$BF_3$ molar ratio in the recycled acid product 14 is about or greater than 2, most of the alcohol from the separation zone 30 is directed to separation unit 20. An alcohol purge stream 40 may be used to maintain and control the quality of the alcohol used to quench the reaction and separate the reaction products in separation unit 20. The hydrocarbon from separation unit 30 may be directed to the reactor via stream 37 or directed to separation unit 20 via stream 38. Fresh hydrocarbon 42 can be added to the process in any number of ways. As shown, fresh hydrocarbon 42 is added to stream 38 which is directed to separation unit 20. A hydrocarbon purge stream 41 may also be necessary.

The esters produced from this invention can find use in a variety of applications including, but not limited to: as a chemical intermediate in the areas of pesticides and herbicides; metal extraction agents; synthetic lubricants; polymerization aid for acrylic acid esters; insect attractants and repellants; industrial fragrances, odorants and cosmetic components; pharmaceutical applications; photographic applications; as a solvent for paints, inks, and the like; as a carrier for agricultural chemicals; and as a octane enhancing fuel component. In all of these end use areas, a very useful feature is that these products will be low or very low or negligible generators of low level atmospheric ozone formed via photochemical reactions.

Motor gasoline, solvents and the like contain various volatile organic compounds (VOC's), which are involved in complex photochemical atmospheric reactions, along with oxygen and nitrogen oxides ($NO_X$) in the atmosphere under the influence of sunlight, to produce ozone. Ozone formation is a problem in the troposphere (low atmospheric or "ground-based"), particularly in an urban environment, since it leads to the phenomenon of smog. Since VOC emissions are a source of ozone formation, motor gasoline manufacture and formulation and solvents for use in paints, inks, etc. are regulated to attain ozone compliance. Historically, governmental regulation of motor gasoline has focused on limiting the volatility of motor gasoline sold in the United States. Currently, motor gasoline volatility is regulated through seasonally limiting motor gasoline Reid Vapor Pressure. A listing of EPA's regulatory motor gasoline RVP limits is found at 40 C. F. R. 80.27, *Controls and Prohibitions on Gasoline Volatility.*

The United States Environmental Protection Agency (EPA) has developed National Ambient Air Quality Standards (NAAQS) for six pollutants: ozone, nitrogen oxides ($NO_x$), lead, carbon monoxide, sulfur dioxide and particulates. Ground-level ozone, a primary component of smog, exceeds target levels in many areas of the United States. The CAA90, for example, includes provisions to reduce urban ozone levels. Reformulated gasoline is targeted to reduce ozone forming hydrocarbon emissions in the United States worst ozone non-attainment areas by 15 percent in 1995 and by 20 percent by 2000. The CAA90 includes several programs to reduce urban ozone including stricter automobile tailpipe emissions limits of 0.25 grams per mile nonmethane hydrocarbons and stricter gasoline Reid Vapor Pressure limits. Therefore, ozone non-attainment has an impact on motor gasoline formulation through regulatory seasonal Reid Vapor Pressure limitations and gasoline reformulation.

According to current VOC emission regulations in the U.S.A., some gasoline components belong to one of two groups depending on their reactivity toward atmospheric photochemical ozone formation:

(a) Negligible reactivity organic compounds which generate about the same or less quantity of ozone as would be produced by the same weight % as ethane. These organic compounds are exempt from the definition of a VOC and are not considered to be a VOC in any fluid composition. There are numerous such compounds exempted by the EPA from the definition of VOC. Other such organic compounds, such as tertiary butyl acetate which is under exemption consideration by the EPA, while having a significantly improved flammability level and evaporation rate, may be too chemically and thermally unstable for motor gasoline applications.

(b) Other oxygenated and hydrocarbon compounds are considered to be VOC's and treated by the EPA as equally (on a weight basis) polluting.

Current regulations based on VOC emissions do not take into consideration the wide difference in ozone formation among non-exempt VOC compounds. For example, two non-exempt VOC compounds can have dramatically different ozone formation characteristics. Accordingly, current regulations do not encourage end users to minimize ozone formation by using low reactivity hydrocarbon compositions.

Hydrocarbon compounds currently viewed as essentially non-ozone producing are those which have reactivity rates in the range of ethane. Ethane has a measured reactivity based on the MIR method of 0.35. In fact, the EPA has granted a VOC exemption to certain solvents with reactivity values in this range including acetone (MIR=0.48) and methyl acetate (MIR=0.12).

However, the number of known materials having reactivities of 0.50 or less based on the MIR scale is relatively small. Moreover, it is a discovery of the present inventors that many if not most of the known fluids having acceptable reactivities with respect to ozone formation have other unfavorable performance characteristics. For example, ethane is a gas under ambient conditions and hence is a poor choice as an industrial solvent. Methyl acetate has an excellent MIR=0.12, but a low flash point of about −12° C.; acetone has an acceptable MIR=0.48, but is extremely flammable. As a further example, tertiary butyl acetate (t-butyl acetate) has an excellent MIR=0.21, but has limited thermal stability.

Among the most preferred fluids according to the present invention are dimethyl carbonate and methyl pivalate. Table 1 demonstrates the extremely low relative reactivities—significantly lower than both acetone and ethane—of methyl pivalate. This data shows that the EPA requirements for exempt solvents in accordance with current VOC regulations and demonstrating extremely low reactivity for the possible future reactivity based rules.

TABLE 1

Summary of calculated incremental reactivities (gram basis) for ethane, acetone, and methyl pivalate, relative to the average of all VOC emissions.

| Scenario | Ozone Yield Relative Reactivities | | | Max. 8 Hour Avg. Relative Reactivities | | |
|---|---|---|---|---|---|---|
| | Ethane | Acetone | Me-Pvat | Ethane | Acetone | Me-Pvat |
| Max React | 0.09 | 0.12 | 0.06 | 0.08 | 0.15 | 0.07 |
| Max Ozone | 0.16 | 0.14 | 0.11 | 0.10 | 0.15 | 0.09 |
| Equal Benefit | 0.21 | 0.15 | 0.12 | 0.12 | 0.15 | 0.09 |

Table 2a shows the conversion of a portion of the data in Table 1 into Absolute Maximum Incremental Reactivities (MIRs) for methyl pivalate. As seen from Table 2a, Absolute Ozone Formation for different levels of $NO_x$ in ROG is highest for highest level of $NO_x$ scenario (MIR) and lowest for lowest level of $NO_x$ scenario (EBIR). As a result, Absolute Reactivity in atmospheric photochemical ozone formation for tested compounds is highest for MIR scenario and lowest for EBIR scenario.

TABLE 2a

Absolute Reactivity Conversion Ratios

| | | ROG | Ethane | Acetone | MP |
|---|---|---|---|---|---|
| Ozone Yield Relative Reactivities | MIR | 1 | 0.09 | 0.12 | 0.06 |
| | MOIR | 1 | 0.16 | 0.14 | 0.11 |
| | EBIR | 1 | 0.21 | 0.15 | 0.12 |
| Ozone Yield Absolute Reactivities | MIR | 3.93 | 0.354 | 0.472 | 0.236 |
| | MOIR | 1.41 | 0.226 | 0.197 | 0.155 |
| | EBIR | 0.82 | 0.172 | 0.123 | 0.098 |

Table 2b shows methyl pivalate as having acceptable flash points, boiling temperature, evaporation rate, low toxicity, good solvency and overall outstanding performance as a versatile environmentally preferred exempt, extremely low ozone formation fluid (solvent) for a very wide range of applications.

The compounds presented in Tables 3–4 show calculated Absolute MIR reactivities for compounds useful as Very Low Polluting Potential Fluids (VLPPF) and Negligibly Polluting Potential Fluids (NPPF). These fluids provide favorable MIR reactivities, a very wide range of evaporation rates, and a wide range of solvency and compatibility with other solvents, polymers, pigments, catalysts, additives, etc., necessary for actual applications. All the compounds listed in the present invention, especially in Tables 2a –4, are very useful as substitute conventional solvents having an Absolute MIR between 1.5 and 3.0 and especially in solvents having high reactivity Absolute MIR greater than 3.0 in atmospheric photochemical ozone formation.

TABLE 2b

Fluid Solvent Properties

| | Acetone | MP |
|---|---|---|
| Boiling Temperature, ° C. | 56 | |
| Viscosity (cps, 20° C.) | 0.33 | 0.74 |
| Specific Gravity | 0.792 | 0.873 |
| Surface Tension | 22.3 | 23.8 |
| Flash Point (° C.) | −20* | 7 |
| Evaporation Ratio to Butyl Acetate | 18 | 2.2 |
| Hansen Solubility Parameter | | |
| Total | 9.2 | 8.1 |
| Nonpolar | 7.6 | 7.2 |
| Polar | 5.1 | 1.8 |
| H-Bonding | 3.4 | 3.1 |
| Toxicity (LD-50, mg/kg) | 5800 | |

*Reflects Varied Reported Literature Data

TABLE 3

Calculated Absolute MIR Reactivities For Negligibly Polluting Potential Fluids

| Compound | Absolute MIR (gram ozone produced/gram fluid) |
|---|---|
| Methyl Pivalate | 0.236 (Actual measured value) |
| Tertiary Butyl Pivalate | 0.324 |

TABLE 4

Calculated Absolute MIR Reactivities For Very Low Polluting Potential Fluids

| Compound | Absolute MIR (gram ozone produced/gram fluid) |
|---|---|
| Ethyl Pivalate | 0.657 |
| Neopentyl Pivalate | 0.700 |
| Isopropyl Isobutyrate | 0.930 |
| Isopropyl Pivalate | 0.971 |

The invention includes a method of reducing atmospheric ozone formation. There currently are two approaches to evaluation of the factors influencing ground level ozone formation. One is based on the total amount of organics emitted into the atmosphere which ultimately combine with nitrogen oxides in a photochemical reaction to form ozone. Based upon this, all organics are treated equivalently and all contribute equally to ozone formation, and for gasoline, RVP is used as the parameter correlating with the amount of total organics released into the air through evaporative pathways. The second approach recognizes that in fact there are significant differences (as much as about two orders of magnitude) in ozone formation for different compounds.

Thus, the first approach is not scientifically as useful as the second approach. To measure specific ozone formation for individual compounds, Maximum Incremental Reactivity (MIR) method is employed. MIR is defined as grams ozone formed under atmospheric photochemical reaction conditions per gram of test substance (compound). Thus, the preferred oxygenated compositions of the instant invention are products whose absolute maximum incremental reactivity (absolute MIR) is below 1.5 g ozone/gram of compound (low), preferably below 1.0 g ozone/gram of compound (very low) or most preferably below 0.5 g ozone/gram compound (negligible).

The invention also includes producing a gasoline fuel containing an ester for use in internal combustion engines, wherein the ester has a Reid Vapor Pressure less than about 4 pounds per square inch. An important factor in determining a compound's ozone formation potential includes the compound's vapor pressure. Compounds with relatively high vapor pressures are more likely to volatilize into the atmosphere from open sources. Potential open sources include, for example, sources from production, distribution, storage and/or combustion of fuels containing oxygenates. The $C_7$ to $C_{14}$ esters according to the invention are expected to have low vapor pressures in comparison to MTBE and some other oxygenates. Preferably, the esters have a RVP less than about 3.5 psi. More preferably, less than about 3.0 or 2.0 psi. For example, Methyl Pivalate has a Reid Vapor Pressure of about 1.6 psi.

The invention further includes a method for reducing atmospheric ozone formation. The method comprising producing a gasoline fuel containing an ester for use in spark-ignition engines, wherein the ester has an absolute MIR <0.5, thereby reducing atmospheric ozone formation caused at least in part by production, distribution, storage and/or combustion of oxygenated fuels as compared to oxygenated fuels containing oxygenates that are photochemically reactive. Certain hydrocarbon compounds have little or no potential to participate in photochemical reactions that result in ozone formation. Well known examples include methane and ethane, which are not considered as photochemically reactive compounds. When a reactivity scale for ozone formation is employed to estimate ozone formation, the contribution to ozone formation derived from the esters of this invention are very small, significantly below that of currently employed oxygenates such as MTBE, TAME, and ethanol. Because of this advantage this enables the gasoline blender to have a wide range for oxygen content based on the esters of this invention, meet RVP requirements and still substantially reduce ozone formation through evaporative emissions. It is even possible to formulate a gasoline using the esters of this invention having essentially no ozone forming potential as based on absolute MIR values.

An important feature of MIR based ozone formation is that compounds which have MIR values equal to or lower than that of ethane (acetone) are considered to be non-polluting in terms of ozone formation. These compounds are under current regulations considered as not contributing to ozone formation. Ethane has an absolute MIR of 0.35 gram ozone/gram ethane. Acetone has been defined by the EPA as exempt under this definition and therefore is also excluded from consideration as an ozone forming compound. Acetone has an absolute MIR of 0.48 (W. P. L. Carter, Preliminary Report to California Air Resources Board under Contract No. 95-308, Aug. 6, 1998). For example, among the esters of this invention, methyl pivalate has an absolute MIR of 0.24 and methyl isobutyrate has an absolute MIR of 0.42.

Many of the esters according to the invention, particularly the esters of lower neoacids, more particularly MP, provide very low reactivity toward ozone formation. The esters are expected to not participate appreciably in photochemical atmospheric reactions. Therefore, many of the esters according to the invention can be considered environmentally preferred components of gasoline fuels.

The present invention is also directed to environmentally preferred fluids and fluid blends, their use as industrial solvents, and to a method of reducing ozone formation in a process wherein at least a portion of a fluid eventually evaporates.

The fluids and fluid blends of this invention have been selected by the present inventors for their actual or potential low reactivity in the complex photochemical atmospheric reaction with molecular oxygen ($O_2$) and nitrogen oxides ($NO_x$) to create ozone.

The present invention provides a means to reduce ozone formation by photochemical atmospheric reactions from a fluid solvent composition which is intended at application conditions to at least partially evaporate into the atmosphere. By properly selecting low reactive components for a fluid solvent composition, ozone formation can be reduced.

For the purposes of the present invention three groups of reduced ozone reactivity fluids and their uses are described: (a) Low Polluting Potential Fluid (LPPF), (b) Very Low Polluting Potential Fluid (VLPPF), and (c) Negligibly Polluting Potential Fluid (NPPF), according to the Absolute MIR numbers as follows:

| Fluid Solvent Designation | Absolute MIR (gm ozone produced/gm fluid) |
| --- | --- |
| Low Polluting Potential Fluid | 1.0–1.5 |
| Very Low Polluting Potential Fluid | 0.5–1.0 |
| Negligibly Polluting Potential Fluid | <0.5 |

Where a composition is a blend of fluids, a weight average MIR (WAMIR) can be calculated as $$\text{WAMIR} = \Sigma W_i * \text{MIR}_i$$

Where Wi is a weight fraction of solvent fluid component i, and MIRi is the absolute MIR value of solvent fluid component i. For the purposes of the present invention, WAMIR will be the preferred method of measuring "ozone formation potential" or OFP.

It is preferred that the fluids and fluid blends also provide at least one other desirable performance property such as high flash point, low particulate formation, suitable evaporation rates, suitable solvency, low toxicity, high thermal stability, and chemical inertness with respect to non-ozone producing reactions, particularly with respect to acids which may be present in coating formulations.

In a particularly preferred embodiment, the fluids are used in a blend with known industrial solvents or other fluids which present an environmental problem with respect to MIR or lack one or more of the aforementioned desirable performance properties, so that the new fluid blends will have lower MIR than they would without the substituted low ozone formation reactivity fluid or have at least one of the aforementioned other desirable performance properties.

The present invention also includes a method of reducing ozone formation from atmospheric photochemical reactions in an application wherein a fluid eventually evaporates, at least partially, into the atmosphere, comprising replacing at least a portion of a fluid having a relatively higher MIR with a fluid having a relatively lower MIR. In the case where a blend results, it is preferred that the weighted average MIR of the blend be similar to or less than the MIR of a Low Polluting Potential Fluid, and most preferably similar to the MIR of a Negligibly Polluting Potential Fluid.

A fluid or fluid blend according to the present invention may be used as a carrier, diluent, dispersant, solvent, or the like. It is preferred that the fluid or fluid blend be used in a stationary industrial process and it is preferred that the process is a non-combustion process. The present invention offers its greatest benefit from the standpoint of safety and health in large-scale industrial or commercial processes, particularly in large scale coating processes or in formulations used in large quantities overall.

The fluids used in accordance with this invention have been selected for their low or reduced ozone formation potential (as reflected in their low or reduced MIR). The ozone formation potential of a composition or fluid solvent may be determined by any scientifically recognized or peer reviewed method including but not limited to, the MIR scale, the $K^{OH}$ scale, smog chamber studies, and modeling studies such as those performed by Dr. William P. L. Carter. Most references in the description of the present invention will be to the Absolute MIR scale measured in grams ozone produced/gram of fluid solvent. By "low MIR" is meant that the fluids have an MIR similar to or less than 1.5 gram of ozone per gram of the solvent fluid. By "reduced MIR" is meant that, in a process according to the present invention, a first fluid is replaced, in whole or in part, by a second fluid, the second fluid having an MIR lower than the first fluid. One of ordinary skill in the art can determine ozone reactivity of a material according to methods in numerous literature sources and tabulated data published in the open literature. It is mentioned that the terms "replace", "replacement", "replacing" and the like used herein are not to be taken as implying only the act of substituting a second fluid (having acceptable MIR as described herein) in a formulation for a first fluid that may have been previously used in that and similar formulation(s), with such first fluid has undesirable MIR as described herein. Rather, the terms are intended to include the formulations themselves comprising a mixture of the first and second fluids, or one or more such second fluid(s) without any of said first fluid(s), as the fluid system of the formulation. In the case where no such first fluid(s) are present, the concept of "replacement" is intended to refer to corresponding formulations that have only such first fluid(s) present instead of such second fluid(s) and therefore have a lower OFP.

The MIR is preferably determined by smog chamber studies, modeling studies, or a combination thereof, but is more preferably determined by "incremental reactivity", and still more preferably by the Absolute MIR.

The MIR of a fluid used in this invention is preferably less than or equal to 1.5 gram of ozone per gram of solvent fluid, more preferably less than or equal to 1.0 gram of ozone per gram of solvent fluid, and most preferably less than or equal to 0.5 gram of ozone per gram of solvent fluid, but the benefits of the present invention are realized if ozone formation is reduced by replacing a first fluid with a second fluid, in whole or in part, wherein the MIR of the second fluid is reduced from that of the first fluid, even if the second fluid has an MIR greater than 1.5 gram of ozone per gram of solvent fluid.

Therefore, it is preferred that the fluid according to the present invention have an MIR less than or equal to 1.50 and more preferably less than or equal to 1.00, still more preferably less than or equal to 0.50. In an even more preferred embodiment, the reactivity in ozone formation is preferably equal to or less than that of acetone and even more preferably equal to or less than that of ethane, by whatever scale or method is used, but most preferably by the MIR scale. Thus, in a more preferred embodiment, the fluid used in a composition according to the present invention will have an MIR less than or equal to 0.50, even more preferably less than or equal to 0.35.

Specifically preferred fluids according to the present invention include:

pivalates such as methyl pivalate (methyl 1,1,1-trimethyl acetate), ethyl pivalate, isopropyl pivalate, t-butyl pivalate (TBP), neopentyl pivalate (NPP), and neopentyl glycol mono pivalate;

isobutyrate compounds such as methyl isobutyrate, isopropyl isobutyrate, neopentyl isobutyrate, and neopentyl glycol mono isobutyrate; and isopropyl neononanoate; pivalonitrile; and methyl 2,2,4,4-tetramethyl pentanoate (methyl neononanoate). Other preferred fluids are oxygenated (oxygen containing) organic compounds substantially free of moieties containing unsaturated carbon-carbon bonds or aromatic groups.

In the case of a blend, the weighted average MIR of the fluids in a composition according to the present invention will also have the preferred, more preferred, and most preferred MIR levels as discussed herein.

In another preferred embodiment, wherein the blend results from replacing part of a first fluid with a second fluid and thereby reducing the weight average MIR, it is preferred that the weight average MIR be reduced 10%, more preferably 25%, still more preferably 50%, from the MIR calculated prior to the fluid replacement.

In yet another preferred embodiment, the Low Polluting Potential Fluids (LPPF), Very Low Polluting Potential Fluids (VLPPF), and Negligibly Polluting Potential Fluids (NPPF), as described herein will provide at least one other desirable performance property such as high flash point low particulate formation, suitable evaporation rates, suitable solvency, low toxicity, high thermal stability, and chemical inertness. Of course, it is more preferable that the fluid or blends have two or more of these performance attributes, and so on, so that the most preferred fluid or fluid blend has all of these performance attributes.

In the case of a process of reducing ozone formation, wherein a fluid according to the present invention replaces a fluid, at least in part, having a higher MIR, described in more detail below, it is preferred that this fluid replacement process, in addition to reducing ozone formation does not negatively impact any other desirable performance attributes of the composition as described above.

The flash point of a fluid according to the present invention is preferably at least −6.1° C. or higher, more preferably greater than +6.0° C., even more preferably greater than 15° C., still more preferably greater than 25° C., yet even more preferably greater than 37.8° C., and most preferably greater than 60° C. One of ordinary skill in the art can readily determine the flash point of a fluid or blend (e.g., ASTM D92-78).

In the case of a blend, the flash point of the blend may be the flash point of the more volatile component, in the instance where the flash points of the individual components differ markedly or where the more volatile component is the predominant component. The flash point of the blend may be in between the flash points of the individual components. As used herein, the term "flash point" will refer to the flash point experimentally determined for a single fluid or a blend, as applicable.

The fluid or blend thereof, according to the present invention, should preferably not contribute measurably to particulate formation of particulates having a size diameter below 2.5 μm—referred to as 2.5 PM herein—in the atmosphere. In a preferred embodiment of a process of reducing ozone formation, the fluid selected to replace a previously-used solvent will be one that also reduces particulate matter to less than or equal to 65 μg/m$^3$, and more preferably less than or equal to 50 μg/m$^3$, when measured over a 24-hour period, preferably spatially averaged over all monitors in a given geographic area.

The evaporation rate should be suitable for the intended purpose. In many if not most applications, the fluid according to the present invention will be used to replace, at least in part, a fluid which is environmentally disadvantaged, meaning it has a reactivity in ozone formation greater than 1.5 in Absolute MIR units. The fluid selected preferably will have a similar evaporation rate to the disadvantaged fluid being replaced, particularly in the case where a fluid blend is used and an acceptable evaporation profile is desired. It is convenient for the fluid selected to have an evaporation rate less than 12 times the evaporation rate of n-butyl acetate. Evaporation rates may also be given relative to n-butyl acetate at 1.0 (ASTM D3539-87). Ranges of evaporation rates important for different applications are 5–3, 3–2, 2–1, 1.0–0.3, 0.3–0.1, and <0.1, relative to n-butyl acetate at 1.0. The present invention is related to fluids and fluid blends that at least partially evaporate into the atmosphere during or after their application. The use of fluids of the present invention is preferred when >25% of the fluid is evaporated, more preferably when >50% of the fluid is evaporated, more preferably when >80% of the fluid is evaporated, more preferably when >95% of the fluid is evaporated, and most preferably when >99% of the fluid is evaporated. In a preferred embodiment of the present invention wherein, in a method of reducing ozone formation, a fluid according to the present invention replaces, at least in part, another fluid not according to the present invention, the fluid replaced has an evaporative rate ranging from that of MEK (methyl ethyl ketone) to less than that of n-butyl acetate.

The fluid or fluid blend according to the present invention may act in the traditional manner of a solvent by dissolving completely the intended solute or it may act to disperse the solute, or it may act otherwise as a fluid defined above. It is important that the solvency of the fluid be adequate for the intended purpose. In addition to the required solvency, the formulated product must be of a viscosity to enable facile application. Thus, the fluid or fluid blend must have the appropriate viscosities along with other performance attributes. One of ordinary skill in the art, in possession of the present disclosure, can determine appropriate solvent properties, including viscosity.

Toxicity relates to the adverse effect that chemicals have on living organisms. One way to measure the toxic effects of a chemical is to measure the dose-effect relationship; the dose is usually measured in mg of chemical per kg of body mass. This is typically done experimentally by administering the chemical to mice or rats at several doses in the lethal range and plotting the logarithm of the dose versus the percentage of the population killed by the chemical. The dose lethal to 50% of the test population is called the median lethal dose (LD50) and is typically used as a guide for the toxicity of a chemical. See, for instance, Kirk-Othmer Encyclopedia of Chemical Technology, Fourth Edition, Vol. 24, pp. 456–490. Currently an LD50 of >500 mg/kg qualifies as "not classified" for oral toxicity under OSHA rules. EU (European Union) uses a cutoff of >2,000 mg/kg. It is preferred that the fluid or fluid blend according to the present invention have an oral rat LD50 of >500 mg/kg, more preferably >1000 mg/kg, still more preferably >2,000 mg/kg, even more preferably >3,000 mg/kg, and most preferably >5,000 mg/kg. Likewise, the fluid or blend should also cause no toxicity problems by dermal or inhalation routes and should also not be an eye or skin irritant, as measured by OSHA or European Union (EU) standards.

As described above, the present invention is related to fluid solvents and fluid solvent blends which produce reduced ozone formation due to atmospheric photochemical reactions and which avoid the deficiencies associated with halogenated organic compounds, particularly toxicity, ozone depletion, incineration by-products and waste disposal problems. In this aspect, the volatile components of the preferred fluid solvents and fluid solvent blends preferably do not have more than 2.0 wt. % of halogen and more preferably less than 0.5 wt. %, and most preferably less than 0.1 wt. %.

The fluid according to the present invention should be thermally stable so that it does not break down. For instance, the material should not break down into reactive species. In a preferred embodiment, the fluid is more thermally stable than t-butyl acetate.

The fluid is preferably inert. As used herein, inert refers to the lack of a tendency to undergo decomposition with other materials in the fluid system. This includes, for example, the lack of a tendency to decompose when combined with acids or bases, and particularly with acid catalysts, which are typically present in coating compositions.

It is preferred that the fluid being replaced have an MIR greater than that of acetone. In another embodiment, the incremental reactivity, based on the MIR scale, of the fluid being replaced is preferably >0.50, still more preferably >0.100, and most preferably >1.50.

In another embodiment, it is critical that in a process of reducing tropospheric ozone formation according to the present invention, the fluid replaced has a greater MIR than the fluid added, that is, the fluid according to the present invention. Of course it is to be recognized that only a portion of the higher MIR fluid need be replaced, thus obtaining a blend, in order to achieve the ozone formation reduction.

However, in another embodiment of the present invention, the fluid being replaced may have an acceptable MIR, but be unacceptable with respect to one or more of the aforementioned performance attributes of flash point or flammability, particulate formation, evaporation rate, solvency, toxicity, thermal stability, or inertness.

Examples of fluids which are replaced by fluids according to the present invention include aromatic and aliphatic hydrocarbon fluids such as: branched $C_6$–$C_9$ alkanes, straight chain alkanes, cycloaliphatic $C_6$–$C_{10}$ hydrocarbons, natural hydrocarbons (alpha or beta pinenes, or turpentines, etc.), ethanol, propanol and higher nontertiary alcohols, $C_3$ and higher ethers, ether alcohols, ether alcohol acetates, ethyl ethoxy propionate, $C_5$ and higher ketones, cyclic ketones, etc., $C_7$+ aromatic hydrocarbons; halocarbons, particularly chlorinated and brominated hydrocarbons; and ethers such as cyclic ethers such as tetrahydrofuran (THF). Examples of other common industrial solvents which may be replaced by fluids according to the present invention are those listed in *Kirk-Othmer Encyclopedia of Chemical Technology, Fourth Edition*, Vol. 22, p. 536–548.

Some particularly preferred replacements, coatings applications, such as replacing methyl pivalate for toluene, xylene, or t-butyl acetate; methyl isobutyrate for xylene or methyl isobutyl ketone (MIBK); and methyl 2,2,4,4-tetramethyl pentanoate for methyl amyl ketone (MAK), propylene glycol monomethyl ether acetate (PMAc), or ethyl ethoxy propionate (EEP).

The fluids and blends according to the present invention may be used in any process using a fluid, and particularly those processes wherein at least a portion of the fluid evaporates and even more particularly wherein at least a portion evaporates into the atmosphere. Preferred processes are those utilizing the fluid as one or more of a carrier, diluent, dispersant, solvent, and the like, include processes wherein the fluid functions as an inert reaction medium in which other compounds react; as a heat-transfer fluid removing heat of reaction; to improve workability of a manufacturing process; as a viscosity reducer to thin coatings to application viscosity; as an extraction fluid to separate one material from another by selective dissolution; as a tackifier or to improve adhesion to a substrate for better bonding; as a dissolving medium to prepare solutions of polymers, resins, and other substances; to suspend or disperse pigments and other particulates; and the like.

It is preferred that the process be a stationary process and also preferred that the process be a non-combustion process. It is particularly beneficial if the fluid according to the present invention be used to replace at least a portion of a traditional industrial solvent in a process using a large amount of fluid, e.g., a process using 1000 lb/year (500 kg/year), even more preferably 5 tons/year (5000 kg/yr), still more preferably 50 tons/year (50,000 kg/yr), and most preferably one million lbs/year (500,000 kg/yr). In a preferred embodiment, the process wherein the aforementioned fluid replacement occurs is on the scale of at least pilot plant-scale or greater.

It is also preferred that the process in which a fluid or blend according to the present invention is used or in which at least one fluid according to the present invention replaces, at least partially, a fluid having a higher MIR, be a process in which the fluid is intended to evaporate, such as in a coating process. In such a process were the fluid is intended to evaporate, it is preferred that at least 10% of the fluid or fluids evaporate, more preferably 20% of the fluids, and so on, so that it is most preferable if >99% of the fluid or fluids present in the coating evaporate.

Furthermore, one of the greatest environmental benefits of replacing a currently-used industrial solvent with a solvent according to the present invention will be realized if performed in a geographic area where monitoring for ozone and particulate matter formation occurs, and more particularly in geographic areas defined by a city and its contiguous area populated by at least 500,000 persons, and wherein the replacement of at least a portion of the currently-used industrial solvent with a fluid according to the present invention causes at least one of:

(i) a reduction in the ozone formation, as measured by either monitoring devices or by a calculation of the reduction using the MIR of the industrial solvent replaced and the fluid added according to the present formation; or (ii) a reduction in particulate formation of particles having a diameter less than 2.5 $\mu$m (2.5 PM), preferably measured as a 24 hour standard, more preferably wherein that reduction is from greater than 65 $\mu$g/m$^3$ to less than that amount in a 24 hour period, still more preferably from greater than 65 $\mu$g/m$^3$ to less than or equal to 50 $\mu$g/m$^3$ in a 24 hour period;

and more preferably both (i) and (ii).

In another embodiment, there is a method of selecting a fluid for use in a process wherein at least a portion of the fluid eventually evaporates into the atmosphere, comprising selecting as the fluid a blend of:

(a) at least one fluid A having a low MIR, preferably similar to or less than or equal to 1.50, more preferably less than or equal to 1.00, yet still more preferably wherein the MIR is less than or equal to 0.50 and still even more preferably less than or equal to 0.35; and (b) at least one fluid B characterized by having at least one unsuitable attribute selected from: (i) high MIR, preferably measured by the MIR scale, e.g., having an MIR>0.50, more preferably >1.00, and yet even more preferably >1.50; (ii) low flash point, preferably less than or equal to 37.8° C., more preferably less than or equal to 25° C., even more preferably less than or equal to 15° C., yet even more preferably less than or equal to 6.0° C., and most preferably less than −6.1° C.; (iii) formation of 2.5 PM particulates (e.g., wherein said process, using fluid B, produces 2.5 PM greater than 65 micrograms per cubic meter or greater, as measured in a 24-hour period); (iv) toxicity, preferably those having an oral rat LD50 less than or equal to 1,000 mg/kg, and most preferably less than or equal to 500 mg/kg; (vi) thermal stability, preferably having a thermal stability equal to or less than (more unstable) than t-butyl acetate; and (vii) inertness in the fluid or fluid blend, particularly with respect to any acids or bases present in the fluid or blend.

Preferred examples of fluid A include:

methyl pivalate for toluene, xylene, or t-butyl acetate; methyl isobutyrate for xylene or methyl isobutyl ketone (MIBK); and methyl 2,2,4,4-tetramethyl pentanoate for methyl amyl ketone (MAK), propylene glycol monomethyl ether acetate (PMAc), or ethyl ethoxy propionate (EEP);

pivalates (trimethyl acetates) such as methyl pivalate (MP), isopropyl pivalate, t-butyl pivalate (TBP), neopentyl pivalate (NPP), and neopentyl glycol mono pivalate;

isobutyrate compounds such as methyl isobutyrate isopropyl isobutyrate, neopentyl isobutyrate, and neopentyl glycol mono isobutyrate; and methyl 2,2,4,4-tetramethyl pentanoate (methyl neononanoate).

Preferred examples of fluid B include aromatic and aliphatic hydrocarbon fluids such as toluene and xylenes; alcohols such as ethanol, n-butyl alcohol, n-propyl alcohol, and sec-butanol; esters such as ethyl ethoxy propionate propylene glycol methyl ether acetate; ketones such as methyl ethyl ketone (MEK), $C_5$–$C_{10}$ linear ketones, cyclic ketones; halocarbons, particularly chlorinated and brominated hydrocarbons; cyclic ethers such as THF, and non-cyclic ethers such as methyl tert-butyl ether (MTBE).

The present invention also concerns mixtures or blends of at least one fluid according to the present invention and fluids which are known to have acceptable low OFP, e.g., acetone (MIR=0.48), methyl acetate (MIR=0.12), tert-butyl acetate (MIR=0.21), tertiary butanol (MIR=0.40), dimethyl succinate (MIR=0.20), dimethyl glutarate (MIR=0.40), and propylene carbonate (MIR=0.43). Such blends can have some important advantages, for example, blends of DMC and MEK, or DMC and methyl acetate, as previously mentioned. These blends are also considered to be part of the present invention. In combination with fluids having an MIR higher than 0.50, the fluids still can provide significant reduction in ozone formation for blended fluid compositions with other important properties for the particular application. Therefore, fluid compositions with low or reduced OFP comprising solvents selected from the list above are important goals of the present invention, even if their weighted OFP is above 0.50 in the MIR scale.

The fluids listed above are recommended to be used in solvent compositions intended for release into air and are required to provide low reactivity in ozone formation. The solvents selected according to the present invention can be used in blends with each other as well as in blends with other solvents (e.g., solvents B, above), different from the solvents of the present invention. When all solvents included in the blend have MIR reactivity ~0.50 or less, the solvent blends also will have low atmospheric photochemical reactivity with MIR of about 0.50 and less.

The present inventors have found that many solvent blends can have an MIR in the range of ethane or acetone, even though one component may exceed that range, and therefore in terms of reactivity toward ozone formation behave as exempt solvents. The range of reactivities in exempt solvents allows a selection of fluids with extremely low reactivity, with MIR number in range of $\leq 0.35$ and more suitably $\leq 0.24$. These fluids can be blended not only with fluids with reactivity based on MIR of ~0.50 or less but, with appropriately selected fluids with MIR numbers >0.50 and at certain ratios still form fluid compositions with weighted reactivity about 0.50 or less. These blends can significantly expand the range of properties of solvent compositions and provide formulators with necessary flexibility for different applications. The selection of fluids with MIRs >0.50 can be relatively wide, however, to achieve significant reduction in weighted reactivity to ~0.50 or less, it is recommended to choose solvent with MIR <1.5, suitably <1.2, and more suitably <1.0.

The conception of blends demonstrating MIR of about 0.50 or less can be applied to other solvents with known extremely low reactivities. For example, methyl acetate has an MIR 0.12 but flash point ~-12° C. Thus, methyl acetate can be blended with butyl acetate (MIR=1.00 and flash point 27° C.) in weight ratio of 57:43 forming a blend with MIR=0.50, providing reactivity similar to exempt solvents. This blend would have a better flash point and lower evaporation rate, making it useful for many applications which methyl acetate could not satisfy due to very low flash point. Butyl acetate which is not an exempt solvent, would become part of a mixture which by its weighted reactivity would behave similar to exempt solvent and, therefore, constitute preferred solvent composition.

This special case of blends comprising at least one solvent with MIR reactivity <0.50 and at least one solvent with MIR>0.50 which have their weighted reactivity about 0.50 or less is one very important part of the present invention. Among known solvents with extremely low MIR, suitable components for the preferred blended solvents are methyl acetate (MIR=0.12), t-butyl acetate (MIR=0.21), dimethyl succinate (MIR=0.20) and methyl siloxanes including cyclomethylsiloxanes. Blends of these solvents with other solvents with MIR>0.50 resulting in weighted MIR of about 0.50 or less for the blend are preferred solvents according to the present invention.

However, some of the most interesting blends are the blends of at least one solvent with MIR reactivity <0.50 and with at least one with MIR reactivity >0.50, which can be generated with the solvents from the list of the present invention.

The present invention offers fluids and fluid blends for use in a variety of industrial applications such as paints and other coatings, adhesives, sealants, agricultural chemicals, cleaning solution, consumer products such as cosmetics, pharmaceuticals, drilling muds, extraction, reaction diluents, inks, metalworking fluids, etc.

The most preferred use of the fluids according to the present invention is with any process wherein the reduction of ozone formation is desired, and more particularly in consumer products, and coatings such as auto refinishing, architectural and industrial coatings and paints.

Paints and coatings comprise the largest single category of traditional solvent consumption, accounting for nearly half the solvents used. Fluids serve multiple functions in paints and coatings, including solubility, wetting, viscosity reduction, adhesion promotion, and gloss enhancement. Fluids dissolve the resins, dyes and pigments used in the coating formulations. Also, prior to application, it is common practice to add solvent thinner to attain the desired viscosity for the particular application. Solvents begin to evaporate as soon as the coating materials are applied. As the solvent evaporates, film formation occurs and a continuous, compact film develops. Single solvents are sometimes used in coatings formulations, but most formulations are blends of several solvents. In many coatings applications, the solvent system includes a slow-evaporating active solvent that remains in the film for an extended period to enhance the film's gloss and smoothness. Because of evaporation and the large amounts of solvents used in coatings, there is a significant amount of VOC emissions into the atmosphere.

Resins which may be incorporated into compositions comprising fluids according to the present invention include acrylic, alkyd, polyester, epoxy, silicone, cellulosic and derivatives thereof (e.g., nitrocellulosic and cellulosic esters), PVC, and isocyanate-based resins. Numerous pigments may also be incorporated into compositions according to the present invention, and it is within the skill of the ordinary artisan to determine proper selection of the resin and pigment, depending on the end use of the coating.

One of the cleaning applications is cold solvent cleaning which is used to degrease metal parts and other objects in many operations. Mineral spirits have been popular in cold cleaning, but are being supplanted by higher flash point hydrocarbon solvents due to emissions and flammability concerns. Efforts to eliminate organic solvents entirely from cleaning compositions have not been successful because aqueous cleaners do not have the performance properties that make organic solvent based cleaners so desirable. This invention allows formulators the option to seek the use of solvents with very low reactivity as environmentally preferred products meeting environmental concerns and customer performance concerns.

A cleaning solution application that uses evaporation to clean is called vapor degreasing. In vapor degreasing, the solvents vaporize and the cold part is suspended in the vapor stream. The solvent condenses on the part, and the liquid dissolves and flushes dirt, grease, and other contaminants off the surface. The part remains in the vapor until it is heated to the vapor temperature. Drying is almost immediate when the part is removed and solvent residues are not a problem. The most common solvent used in vapor degreasing operations has been 1,1,1-trichloroethane. However, since 1,1,1-trichloroethane is being phased out due to ozone depletion in the stratosphere, alternatives are needed. Moreover, chlorine-based solvents have toxicity concerns. Thus, some of the low reactivity, high flash point solvents in this invention can be used in place of 1,1,1-trichloroethane and other halogenated solvents.

An application that is similar to coatings is printing inks. In printing inks, the resin is dissolved in the solvent to produce the ink. Most printing operations use fast evaporating solvents for best production speeds, but the currently used solvents are highly reactive. Some of the previously described fast evaporation, high flash point, low reactivity in ozone formation fluids according to the present invention are suitable for printing inks.

An application that is suitable to the low toxicity, high flash point and low reactivity in ozone formation fluids according to the present invention is agricultural products. Pesticides are frequently applied as emulsifiable concentrates. The active insecticide or herbicide is dissolved in a hydrocarbon solvent, which also contains an emulsifier. Hydrocarbon solvent selection is critical for this application. It can seriously impact the efficiency of the formulation. The solvent should have adequate solvency for the pesticide, promote good dispersion when diluted with water, have low toxicity and a flash point high enough to minimize flammability hazards.

Extraction processes, used for separating one substance from another, are commonly employed in the pharmaceutical and food processing industries. Oilseed extraction is a widely used extraction process. Extraction-grade hexane is a common solvent used to extract oil from soybeans, cottonseed, corn, peanuts, and other oil seeds to produce edible oils and meal used for animal feed supplements. Low toxicity, high flash point, low MIR fluids and fluid blends of the present invention can be useful in such industries.

In addition to the above-mentioned applications, other applications that can use high flash point, low toxicity, low reactivity in ozone formation fluids are adhesives, sealants, cosmetics, drilling muds, reaction diluents, metal working fluids, and consumer products, such as pharmaceuticals or cosmetics.

The invention is further described in the following examples, which are intended to be illustrative and not limiting. One of skill in the art will recognize that numerous variations are possible within the scope of the appendaged claims.

EXAMPLES OF FLUID BLENDS HAVING NEGLIGIBLE REACTIVITY

Tables A and B below demonstrate fluid solvent blends may be created using (a) negligibly low reactivity fluid solvents and (b) low to very low reactivity fluid solvent in ratios which provide Weight Average MIR reactivity for the total solvent blend of <0.45 and therefore providing ozone formation similar to individual fluid solvents with negligibly low reactivity in atmospheric ozone formation. However, the blends shown in Tables A and B possess characteristics such as better evaporation profiles, flash points, as compared to the individual fluids.

Table A demonstrates negligibly reactive blends based on a known negligibly reactive solvent—methyl acetate and other very low reactivity fluids previously known and from the present invention. In Table A the column with methyl acetate shows the minimum methyl acetate content that will provide negligible reactivity to the blend. As shown, all blends with increased methyl acetate content will result in reduced reactivity in ozone formation.

However, a main interest in blends with reduced methyl acetate content that maintain negligible reactivity is in an increased flash point of the blend. As seen from Table A, especially advantageous are the blends with the very low reactivity fluid solvents from the present invention, ethyl pivalate, which require the lowest levels of methyl acetate. This concept of blending the negligible reactivity compounds with low and very low reactivity secondary fluids that can provide Weight Average MIR less than 0.5 is also subject of this invention.

Although it is not necessary that every component of the blend be selected from the list of compounds of the present invention, it should be noted that components selected from the list of the present invention provide especially desirable attributes to a finished solvent blend with reduced or negligible reactivity in atmospheric photochemical ozone formation.

Advantages of the blends created with at least one compound of the present invention is further demonstrated in Table B which utilizes blends with DMC as the negligible reactivity component. DMC allows a high level of the use of the second fluid while maintaining a low MIR while still providing a fluid solvent with an increased flash point from the second fluid by itself. The flash points of each of the composition blends in Table B are >+6° C. and the majority of them have flash points >+15 GC.

TABLE A

Selected Blends of Methyl Acetate with Other Very Low Reactivity Solvents at Absolute MIR = 0.45

| Very Low Reactivity Solvent (Second Fluid Solvent) | Absolute MIR of Second Fluid Solvent | Weight % of Second Fluid Solvent in Blend with Absolute MIR = 0.45 | Weight % of Methyl Acetate in Blend with Absolute MIR = 0.45 |
|---|---|---|---|
| Decane | 0.93 | 40.7 | 59.3 |
| Undecane | 0.82 | 47.1 | 52.9 |
| Dodecane | 0.72 | 55.0 | 45.0 |
| Tridecane | 0.66 | 61.1 | 38.9 |
| Ethyl Propionate | 0.86 | 44.6 | 55.4 |
| Isobutyl Isobutyrate | 0.86 | 44.6 | 55.4 |
| Diacetone Alcohol | 0.96 | 39.3 | 60.7 |
| diisopropyl Carbonate* | 0.606 | 67.9 | 32.1 |
| Ethyl Pivalate* | 0.657 | 61.5 | 38.5 |

*Compounds of the present invention

TABLE B

Selected Blends of DMC* with Other Low or Very Low Reactivity Solvents at Absolute MIR = 0.45 With Flash Points >+6° C.

| Low or Very Low Reactivity Solvent (Second Fluid Solvent) | Absolute MIR of Second Fluid Solvent | Weight % of Second Fluid Solvent in Blend with Absolute MIR = 0.45 | Weight % of DMC in Blend with Absolute MIR = 0.45 |
|---|---|---|---|
| Methyl Ethyl Ketone | 1.32 | 29.9 | 70.1 |
| Isopropanol | 0.81 | 50.8 | 49.2 |
| Decane | 0.93 | 43.6 | 56.4 |
| Butyl Acetate | 1.14 | 35.0 | 65.0 |
| Isopropyl Isobutyrate | 0.86 | 47.5 | 52.5 |
| diisopropyl Carbonate* | 0.606 | 70.4 | 29.6 |
| Ethyl Pivalate* | 0.657 | 64.2 | 35.8 |

*Compounds of the present invention

Example 1

A representative solvent/resin system was chosen to evaluate the sensitivity of a system to solvent changes and evaporation rate differences. Sequential changes to the solvent system were made, and the impact on resin solubility and evaporation rate profile was determined.

The initial system contained of 30 wt % Acryloid B-66 resin (an acrylic resin available from Rohm & Haas) in a fluid mixture comprised of 40 wt % MEK (methyl ethyl ketone), 40 wt % MIBK (methyl isobutyl ketone), and 20 wt % Exxate® 600 (a $C_6$ alkyl acetate available from Exxon-Mobil Chemical Company). Methyl pivalate was substituted in increments for MIBK, while keeping the rest of the system constant. For example, a solvent blend of 40 wt % MEK, 35 wt % MIBK, 5 wt % MP and 20 wt % Exxate®

600 was evaluated, and so on until the final solvent blend consisted of 40 wt % MEK, 0 wt % MIBK, 40 wt % MP and 20 wt % Exxate® 600. This same procedure was repeated substituting methyl pivalate for MEK, while keeping the rest of the solvent system the same. Ultimately, a solvent blend in which both the MEK and MIBK were replaced by methyl pivalate (i.e., 80 wt % methyl pivalate and 20 wt % Exxate® 600) was considered. Evaporation profiles were compared for each solvent blend.

The time required to evaporate 10, 50, and 90 wt % of the fluid was calculated using CO-ACT$^{SM}$ computer program (see, for instance, Dante et al., *Modern Paint and Coatings*, September, 1989). The results are shown in Table 5.

TABLE 5

| Wt % in fluid | Evaporation (minutes) | | | MIR |
|---|---|---|---|---|
| (w/20 wt % Exxate ® 600) | 10% | 50% | 90% | Reduction |
| 40 MEK/40 MIBK | 0.7 | 4.9 | 46 | (comparative) |
| 40 MEK/0 MIBK/40 MP | 0.5 | 3.5 | 44 | 68% |
| 0 MEK\40 MIBK/40 MP | 0.9 | 6.3 | 48 | 17% |

The reduction in MIR is calculated using the known values of 1.34 for MEK, 4.68 for MIBK, and determined values of 0.236 for methyl pivalate (MP).

These results show that there is very little difference in the evaporation profiles between a known resin/solvent system and a resin/solvent system using the fluids according to the present invention. Moreover, the above results show the advantage of the process according to the present invention of reducing ozone formation by replacing at least a portion of a fluid not having a low ozone formation potential (MIR>0.50) with a solvent exhibiting a low reactivity in ozone formation.

Example 2 (Comparative)

The above experiment was repeated using fluids known to have low reactivity in ozone formation, methyl acetate (MeOAc, MIR=0.12) and t-butyl acetate (t-BuOAc, MIR=0.21). The results are shown in Table 6.

TABLE 6

| Wt % in fluid | Evaporation (minutes) | | | MIR |
|---|---|---|---|---|
| (w/20 wt % Exxate ® 600) | 10% | 50% | 90% | Reduction |
| 40 MEK/40 MIBK | 0.7 | 4.9 | 46 | (comparative) |
| 40 MEK/0 MIBK/40 MeOAc | 0.2 | 1.6 | 44 | 69% |
| 0 MEK/40 MIBK/40 MeOAc | 0.2 | 2.9 | 47 | 19% |
| 40 MEK/0 MIBK/40 t-BuOAc | 0.5 | 3.5 | 44 | 68% |
| 0 MEK/40 MIBK/40 t-BuOAc | 0.9 | 6.2 | 48 | 17% |

The results do show a marked effect in the evaporation profile when MeOAc is substituted for MEK or MIBK, and thus this known low OFP fluid would not be a good substitute for currently used coating fluids. While t-BuOAc shows a similar profile to MP, as discussed above t-BuOAc is thermally unstable, and is not inert with respect to acids, as shown below.

Example 3

Acrylic solvent systems were prepared to test the stability of methyl pivalate to acid catalysts, which are commonly present in coating compositions. The formulations contained 29.9 wt % MP, 28.7 wt % pentyl acetate, 20.2 wt % n-butyl acetate, 16.1 wt % n-butyl alcohol, 3.6 wt % methyl ethyl ketone, 1.5 wt % isopropyl alcohol. 2 wt % toluene as an internal standard. The latter materials were purchased from Aldrich Chemical Co.

Para toluene sulfonic acid (pTSA) was added to the above formulation (again, pTSA was purchased from Aldrich Chemical Co.), in the amount of 0.5 wt %. The solutions were sealed and placed in an oven at 50° C. under a nitrogen atmosphere. Samples were withdrawn at intervals for testing. The content of methyl pivalate was monitored over time by gas chromatographic analysis using an HP 5890 gas chromatograph. In a parallel experiment an equal amount of tert butyl acetate was used instead of methyl pivalate. The results are shown below in Table 7 (all percentages are by weight).

TABLE 7

| Solvent | Wt. % of Solvent At Start of Test | Wt. % of Solvent At One Week Decomposition Period | Wt. % of Solvent At Three Week Decomposition Period |
|---|---|---|---|
| MP wt. % | 100 | 88.0 | 65.1 |
| Tert. Butyl Acetate* | 100 | 65.9 | 24.1 |

*decomposes to isobutylene (48.3 wt. %) and acetic acid (51.7 wt. %)

It is interesting to note that the decomposition products of tert butyl acetate, isobutylene and acetic acid, have MIRs of 6.81 and 0.67 respectively. This results in a weight average reactivity of the decomposition products of tert. butyl acetate to be 3.64 grams of ozone produced per gram of decomposition products versus 0.21 per tert butyl acetate. Such decomposition products would not be considered negligible or low reactivity compounds. The decrease in methyl pivalate amount reflects transesterification rather than decomposition chemistry.

The above results clearly show that methyl pivalate is more stable to acid catalysts than is t-butyl acetate. Thus, a coating formulation containing methyl pivalate as a fluid would be expected to be more storage stable than one containing t-butyl acetate. Storage stability is an important attribute in a coating composition, e.g., a paint.

Example 4 (Comparative)

A typical acrylic-based coating system was prepared using a Gloss White Electrostatic Spray Topcoat, formulation MKY-504-1 developed and recommended by S. C. Johnson Polymer as follows:

| Johcryl 504 | 410.62 gr. (80% conc. in xylene) |
| Cymel ™ 303 | 140.94 gr. |
| TiO$_2$ (TiPure R-960) | 360.68 gr. |
| BykP-1049 | 2.22 gr. |
| 10% DC-57 in MAK | 11.10 gr. |
| Nacure 2500 | 5.55 gr. |
| Amyl Acetate | 78.8 gr. |
| Butyl Acetate | 55.49 gr. |
| N-Butanol | 44.39 gr. |

This Composition had the following formula constraints:

| Viscosity (Ford #4) | 44 seconds |
| PVC | 10.2% |
| Weight Solids | 75% |
| Resistivity | 0.7 megaohms |
| VOC | 2.78 lb./gal. |

-continued

| | |
|---|---|
| P/B Ratio | 0.76 |
| Volume Solids | 61.7% |
| Catalyst Level | 0.3% on TRS |

The total solvent composition of the formulation was as follows:

| | |
|---|---|
| Xylene | 29.9 wt. % |
| Amyl Acetate | 28.7 wt. % |
| Butyl Acetate | 20.2 wt. % |
| N-Butanol | 16.1 wt. % |
| MAK | 3.6 wt. % |
| IPA | 1.5 wt. % |

Additional data was calculated for the formulation:

| | |
|---|---|
| Surface Tension .25° C. | 27.12 dyn/cm |
| Flash Point: Deg. C. | 19.5 (Deg. F. 67.1) |

The calculated Evaporation Profile for the formulation characterized in minutes for portions of solvents as it evaporates was as follows:

| | 10% | 50% | 80% | 90% |
|---|---|---|---|---|
| Time (min.) | 4.7 | 33 | 90 | 160 |

This composition was a base to demonstrate how substitution of different component of solvent composition would effect VOC, ozone formation, flash point, and evaporation profile. To calculate ozone formation (in lbs. of ozone per gallon of solid coatings), the following Absolute MIR values from published sources referenced above and our data for the solvents suggested in the present invention were used:

| Component | Absolute MIR |
|---|---|
| Xylene | 7.81 |
| N-Butyl Alcohol | 3.53 |
| N-Butyl Acetate | 1.14 |
| Amyl Acetate | 1.16 |
| Isopropyl Alcohol (IPA) | 0.81 |
| Methyl Amyl Ketone (MAK) | 2.65 |

Wt. Average Absolute MIR for the solvent composition above was calculated to be 3.57 lbs. ozone per lb. of solvent composition, or, multiplying by VOC=2.78 lb./gal. equates to 9.935 lbs. of ozone per gal. of paint.

Example 5

Using the same control formulation as in Example 4 above, methyl pivalate (MP) was substituted for the xylene in the formulation. The replacement solvent composition was as follows:

| | |
|---|---|
| MP | 29.9 wt. % |
| Amyl Acetate | 28.7 wt. % |
| Butyl Acetate | 20.2 wt. % |
| N-Butanol | 16.1 wt. % |
| MAK | 3.6 wt. % |
| IPA | 1.5 wt. % |

The Negligibly Polluting Potential Fluid solvent MP can be removed from VOC, providing 29.9% VOC reduction to VOC=1.95 lb/gal.—a very strong VOC reduction which would be difficult to achieve by conventional reformulation.

The surface tension, flash point, and evaporation profile were calculated to be:

| | | | | |
|---|---|---|---|---|
| Surface Tension | 26 dyn/cm | | | |
| Flash Point Deg. C. | 19.7 (Deg. F. 67.5) | | | |
| Evaporation Profile: | 10% | 50% | 80% | 90% |
| Time (min.) | 3.3 | 26 | 90 | 175 |

As seen from the data, substitution of xylene with MP did not alter the Evaporation Profile significantly or cause any negative effect on the properties of the composition.

Using the Absolute MIR reactivity from Table 2a, the Wt. Avg. MIR reactivity was calculated for the solvent composition to be 1.312. Multiplying the MIR by the VOC of 2.78 lb/gal, it is calculated to be 3.65 lbs. of ozone per gal. of solid coating or 63.3% reduction in ozone formation as compared with control composition.

These examples demonstrate that methyl pivalate and the compounds suggested by the present invention unexpectedly provided not only a very significant reduction in VOC in a typical coating formulation, but also provided incomparably stronger reduction in ozone formation potential. These very strong positive effects were achieved without any negative effect on the coating compositions.

Example 6

Using the same control formulation as in Example 4 above, the replacement solvent composition substituted MP for the xylene, DIPC for the MAK, and a partial substitution of Amyl Acetate with DIPC.

Solvent Composition:

| | |
|---|---|
| MP | 29.9 wt. % |
| DIPC | 23.8 wt. % |
| Amyl Acetate | 8.5 wt. % |
| Butyl Acetate | 20.2 wt. % |
| N-Butanol | 16.1 wt. % |
| IPA | 1.5 wt. % |

The VOC reduction for the composition would be 1.95 lb/gal, as in Example 5.

The surface tension, flash point, and evaporation profile were calculated to be:

| | | | | |
|---|---|---|---|---|
| Surface Tension | 27.16 dyn/cm | | | |
| Flash Point Deg. C. | 35.5 (Deg. F. 95.9) | | | |
| Evaporation Profile: | 10% | 50% | 80% | 90% |
| Time (min.) | 4.0 | 32 | 100 | 195 |

The data demonstrates insignificant change in the Evaporation Profile and no negative effects on the properties of the composition.

Applying to the solvent composition the Absolute MIR reactivity as Wt. Avg. Absolute MIR for the solvent composition of 1.125, or, multiplying by the VOC=2.78 lb/gal results in an MIR value of 3.23 lbs. of ozone per gal. of coating, or 67.5% reduction in ozone formation as compared with the control composition.

Examples 5 and 6 demonstrate important opportunities to reduce ozone formation through the substitution of high reactivity conventional components of the solvent (fluid) composition exclusively with the Negligibly Polluting Potential and Very Low Polluting Potential fluids from the present invention.

However, an important objective of the present invention is the combinations with other known Low Polluting Potential or Very Low Polluting Potential fluid solvents with Negligibly Polluting Potential, Very Low Polluting Potential, or Low Polluting Potential fluid solvents of the present invention.

These combinations can provide the additional reduction in ozone formation potential unattainable by a currently known technology.

Analyses of the composition of Example 6 shows that this system contains N-Butanol which has an Absolute MIR=3.53.

This alcohol is necessary to provide storage stability of the compositions containing hexamethoxymethylmelamine (HMMM) crosslinking agents (Cymel™ 303) and acid (or blocked acid) catalysts. This material cannot be effectively substituted with a non-hydroxyl bearing solvent.

To provide further reduction in ozone formation for the solvent compositions comprising $C_4$ and higher alcohols and ether alcohols, the alcohol functional components can be substituted with methanol and or isopropanol. These hydroxyl functional components have very low reactivity in atmospheric photochemical ozone formation. Due to the toxicity concerns regarding methanol, the preferred choice is isopropanol. The quantity of the alcohols can vary and needs to be optimized for specific formulations, however, mole per mole ratio can be used as a starting point for optimization.

Example 7

Using the same control formulation as in Example 4 above, the replacement solvent composition substituted MP for the xylene, DIPC for the MAK, a partial substitution of Amyl Acetate with DIPC, and IPA for the N-Butanol.

Solvent Composition:

| | |
|---|---|
| MP | 29.9 wt. % |
| DIPC | 23.8 wt. % |
| Amyl Acetate | 11.5 wt. % |
| Butyl Acetate | 20.2 wt. % |
| IPA | 14.6 wt. % |

The VOC for the composition is 1.95.

The surface tension, flash point, and evaporation profile were calculated to be:

| | | | | |
|---|---|---|---|---|
| Surface Tension | 27.02 dyn/cm | | | |
| Flash Point: Deg. C. | 34.1 (Deg. F. 93.4) | | | |
| Evaporation Profile: | 10% | 50% | 80% | 90% |
| Time (min.) | 2.3 | 22 | 100 | 195 |

The data also demonstrates acceptable Evaporation Profile and overall good properties for the coating composition. The WtAv AMIR for the composition is 0.697 or 0.697× 2.78=1.938 lbs. of ozone per gal. of paint. This would represent an 80.5% reduction in ozone formation as compared with the control composition.

Example 8

Using the same control formulation as in Example 4 above, the replacement solvent composition substituted acetone, a solvent having an MIR similar to the Negligibly Polluting Potential Fluids of the present invention, for the xylene.

Solvent Composition:

| | |
|---|---|
| Acetone | 29.9 wt. % |
| Amyl Acetate | 28.7 wt. % |
| Butyl Acetate | 20.2 wt. % |
| N-Butanol | 16.1 wt. % |
| MAK | 3.6 wt. % |
| IPA | 1.5 wt. % |

The surface tension, flash point, and evaporation profile were calculated to be:

| | | | | |
|---|---|---|---|---|
| Surface Tension | 25.76 dyn/cm | | | |
| FlashPoint: | Deg. C. 11.1 (Deg. F. 52.0) | | | |
| Evaporation Profile: | 10% | 50% | 80% | 90% |
| Time (min.) | 1.1 | 18 | 83 | 164 |

The data demonstrates an unacceptable flash point reduction and a very fast evaporation rate, up to 50% of evaporation, which makes the solvent composition unacceptable for commercial applications. The VOC of the coating composition is 1.95 lb/gal., but the flash point and evaporation rate prevent the use of the acetone as an acceptable Negligibly Polluting Potential Fluid of the present invention in an industrial application.

Example 9

A cold-cleaning solvent comprising about 10–60 wt % fluorocarbon, about 1–30 wt % of a chlorinated solvent, and about 10–40 wt % of an oxygenated organic solvent is disclosed in U.S. Pat. No. 5,552,080. The oxygenated organic solvent is preferably n-butanol or isopropanol, but may be also selected from numerous other oxygenated organic fluids, including DMC.

The present inventors have surprisingly discovered that fluids from to the present invention may be used in the aforementioned cleaning composition to reduce tropospheric ozone formation, which is the opposite phenomenon from ozone depletion. This is completely unexpected.

Example 10

The delivery of seed coatings including insecticides and other pesticides, and agents attenuating the growth of plants (e.g., hormones) is extremely valuable to the agricultural industry. In addition to traditional coating techniques, the OSIT method (Organic Solvent Infusion Technique) has been studied and may be useful in the germination of hard coated seeds. In this method, the seed is soaked in the solvent for a fixed amount of time. The solvents are generally highly volatile solvents such as xylene, acetone, methylene chloride ($CH_2Cl_2$). This technique has also been studied in the context of translocation experiments for the production of transgenic crops.

The substitution of MP for MEK results in a similar evaporation profile, while greatly reducing the MIR of the fluid used, in the case of xylene (p-xylene has the lowest MIR of the xylenes, at MIR=4.40) and acetone (MIR=0.48), and having a reduced toxicity in the case of $CH_2Cl_2$ (MIR=0.10).

The examples presented herein demonstrate several beneficial aspects of the inventions:

(a) Fluids with negligibly low MIR reactivity values (<0.5 gr ozone produced/gr solvent fluid used) can be produced using specific chemical compounds (as it demonstrated in literature and in the present invention) and by proper blending with extremely low MIR reactivity organic compounds, preferably methyl acetate and, especially DMC. The blends not only significantly expand the range of negligibly reactive compounds, but also expand the range of properties, and, especially, evaporation profile, which is always significantly wider for blends, than for individual compounds. This is a principal advantage of blends that are deemed Negligibly Polluting Potential Fluids.

(b) The use of Negligibly Polluting Potential Fluids of the present invention provide potential for very significant VOC reduction of the typical solvent compositions. However, reduction of ozone formation with the substitution a part of any solvent with the Negligibly Polluting Potential Fluids of the present invention is disproportionately greater than VOC reduction (~65% versus ~30%). The data demonstrate that VOC is a very poor indicator of ozone formation and can provide misleading data concerning actual ozone formation.

(c) The use of Negligibly Polluting Potential Fluids or any exempt solvents, even with highly beneficial compounds of the present invention provides significant, but still limited reduction in ozone formation.

Further, the use of Low Polluting Potential Fluids and, especially, Very Low Polluting Potential Fluids in solvent fluids as described herein additionally provides very significant reduction in ozone formation which can not be achieved when the use of Negligibly Polluting Potential Fluids is limited by their properties. It should be also said, that use of Very Low Polluting Potential Fluids alone cannot also provide the maximum reduction in ozone formation.

However, synergistic effects providing the best reduction in ozone formation can be achieved by combining properly selected Low Polluting Potential Fluids, Very Low Polluting Potential Fluids, and Negligibly Polluting Potential Fluids. This conclusion is not limited to the specific structures of LPPF, VLPPF, and NPPF discovered by the inventors of the present invention, but also achievable with the known in the art LPPF, VLPPF, and NPPF.

As seen from examples, the use of NPPF provided ozone formation reduction to 63–65%. Addition of very low reactivity fluids provided additional reduction to 80–81% as demonstrated in the examples.

These results were achieved without additional VOC reduction which demonstrate that VOC does not correlate with ozone formation. Additionally, there is a tremendous potential in using the present invention to achieve very significant environmental benefits.

Example 11

A 150 cc magnetic stirring type Hastelloy C autoclave was charged with methanol (47.1 g, 1.47 mole) and phosphoric acid (18.0 g, 0.184 mole) with nitrogen pressure. The nitrogen overpressure was released and boron trifluoride (50.0 g, 0.735 mole) was introduced to the well stirred (2050 rpm), chilled water cooled methanol/phosphoric acid solution. CO was added to the autoclave until the total pressure in the autoclave was 988 psi. The reaction solution was heated to 122° C.

MTBE (21.03 g, 0.24 mole) was added to the autoclave over a period of 32 minutes at 122° C. to 125° C. The pressure in the autoclave during this time varied from 1215 to 1203 psi. CO consumed during the reaction was replenished so as to maintain a relatively constant pressure in the autoclave. Following the complete addition of the MTBE to the autoclave, stirring was continued at 125° C. at 1203 psi for 30 minutes.

The reaction mixture was cooled to 15° C., and the carbon monoxide overpressure was released. The resulting reaction mixture (136.4 g) was added slowly to cooled methanol (135 g, 4.22 mole). The methanol was maintained at 5° C. to 15° C. with an ice bath.

Following the dilution of the reaction mixture with methanol, the diluted reaction mixture was extracted with octane (3×30 ml). The combined octane extracts (71.1 g) were analyzed by gas chromatography (GC). GC analysis indicated methyl pivalate (MP) (2.68 g, 0.023 mole), nonanoic acid methyl esters (NA) (2.29 g, 0.013 mole) and tridecanoic acid methyl esters (TDA) (0.57 g, 0.0025 mole).

The volatile components were removed from the acid product using a film evaporator operated at 1 mm and a temperature of 50° C. The volatile components (123.3 g) were collected in a dry ice/methanol cooled receiving flask followed by two dry ice/methanol cooled traps and were analyzed by GC. GC revealed MP (8.29 g, 0.071 mole) and NA (0.62 g, 0.0035 mole). A methyl pivalate selectivity of 83% was obtained. The clear, red liquid acid product (130.2 g) remaining was used in Example 12 as the source of the acid catalyst. The data of this example are summarized in Table 8.

Example 12

The acid product (130.2 g) containing the acid catalyst from Example 11 was added to an autoclave with nitrogen pressure. The nitrogen overpressure was released and CO was added to 960 psi. The contents of the autoclave were heated to 125° C., at which time the pressure in the autoclave was adjusted to 1205 psi by adding additional CO. MTBE (22.6 g, 0.257 mole) was added over a period of 31 minutes. During this addition period, a pressure increase was observed to 1299 psi. Following the complete addition of MTBE, stirring (2100 rpm) was continued at 125° C. for 90 minutes. CO was consumed during this heating period as observed by a pressure drop to 1209 psi in the autoclave.

The reaction mixture was cooled to 13° C., and the CO overpressure was released. The resulting reaction mixture added slowly into a 250 ml separatory funnel, and two phases separated. The hazy, light yellow upper phase (4.02 g) and a lower predominant phase (146.4 g). The lower acid phase was added slowly to chilled methanol (135.0 g, 4.22 mole) at 5–20° C. GC analysis of the upper phase revealed methyl pivalate (0.08 g, 0.0007 mole) and nonanoic acid methyl esters (4.68 g, 0.02043 mole).

Following the dilution with methanol, the lower phase was extracted with octane as in Example 11. GC analysis of the combined octane phases revealed methyl pivalate (1.47 g, 0.0126 mole), nonanoic acid methyl esters (3.78 g, 0.0211 mole) and tridecanoic acid methyl esters (3.37 g, 0.0147 mole).

The volatile components were removed from the acid product using a film evaporator operated at 30 mm and a temperature of 90° C. The volatile components (155.9 g) were analyzed by GC. The GC analysis indicated methyl pivalate (4.22 g, 0.0364 mole), nonanoic acid methyl esters (2.77 g, 0.0155 mole) and tridecanoic acid methyl esters (0.77 g, 0.00334 mole). Methyl pivalate selectivity dropped to 37.0%. It is believed the acid product from Example 11 was not concentrated sufficiently, thus a relatively weaker catalyst was used in Example 12. The clear, deep red liquid acid catalyst solution (101.76 grams) was used in Example 13. The data of this example are summarized in Table 8.

Example 13

The procedures of Example 12 were repeated with the exception that MTBE (22.61 g, 0.257 mole) was added in 33 minutes. CO was consumed during the addition of MTBE. Following the complete addition of MTBE, stirring was continued at 123° C. and 1211 psi carbon monoxide pressure for 5 minutes. The reaction mixture was cooled to 15° C., and the CO overpressure was released. The resulting reaction mixture (117 g) was slowly added to chilled methanol (135 g, 4.2 mole).

In this Example octane was not added to the diluted reaction mixture. The volatile components were removed using a film evaporator operated at 30 mm and 90° C. The trapped volatile components (150.5 g) were analyzed by GC. GC analysis indicated methyl pivalate (18.26 g, 0.1574 mole) and nonanoic acid methyl esters (4.13 g, 0.0231 mole). The selectivity to methyl pivalate was about 87%. The clear, red acid catalyst solution (98.6 g). 88.5 g of this solution was used in Example 14. The data of this example are summarized in Table 8.

Example 14

The procedures of Example 12 were repeated with the exception that MTBE (19.18 g, 0.218 mole) was added in 26 minutes at 107° C. to 110° C. During the addition of MTBE a pressure increase from 1209 psi to 1235 psi was observed. Following the complete addition of the MTBE, the reaction mixture was stirred at 110° C. for 5 minutes. A pressure drop from 1235 psi to 1224 psi was observed.

The reaction mixture was cooled to 15° C., and the CO overpressure was released. The resulting reaction mixture (101.4 g) was added slowly into chilled methanol (135 g, 4.22 mole). Two phases were observed after dilution with methanol. The two phases were separated in a 500 ml separatory funnel. The upper hazy, yellow phase (2.8 g) was separated and analyzed by GC. GC analysis indicated MTBE (0.0038 g, 0.000044 mole), methyl pivalate (0.043 g, 0.000371 mole), nonanoic acid methyl esters (2.06 g, 0.01151 mole), tridecanoic acid methyl esters (1.95 g, 0.008524 mole), heptadecanoic acid methyl esters (0.54 g, 0.00194 mole), triisobutylene (0.28 g, 0.0017 mole) and tetraisobutylene (0.26 g, 0.0012 mole). The lower acid product (232.4 g) was transferred to a distillation flask for distillation. The volatile components (147.24 g) were removed from the acid product at 30 mm and 90° C. GC analysis indicated MTBE (0.74 g, 0.0084 mole), methyl pivalate (3.56 g, 0.0307 mole), nonanoic acid methyl esters (3.55 g, 0.0199 mole), and tridecanoic acid methyl esters (0.398 g, 0.00174 mole). The remaining clear, red acid product weighed 82.3 g and was analyzed as predominately $BF_3.2CH_3OH$. At a reaction temperature of 110° C., methyl pivalate selectivity decreased to 27.5%. The data of this example are summarized in Table 8.

Example 15

The procedures of Example 11 were repeated with the exception that no phosphoric acid was added. GC analysis of the octane extracts revealed methyl pivalate (3.13 g, 0.027 mole), nonanoic acid methyl esters (1.98 g, 0.011 mole) and tridecanoic acid methyl esters (0.35 g, 0.0015 mole). GC analysis of the volatile components recovered from the acid product revealed methyl pivalate (8.534 g, 0.074 mole), nonanoic acid methyl esters (0.55 g, 0.0031 mole) and tridecanoic acid methyl esters (0.0073 g, 3.19E-05 mole). The data of this example are summarized in Table 8.

Example 16

The procedures of Example 11 were repeated with the exceptions that no phosphoric acid was added and the run temperature was 150° C. GC analysis of the octane extracts revealed methyl pivalate (3.48 g, 0.03 mole) and nonanoic acid methyl esters (0.57 g, 0.0032 mole). GC analysis of the volatile components recovered from the acid product indicated methyl pivalate (8.43 g, 0.073 mole) and nonanoic acid methyl esters (0.06 g, 0.00033 mole). The data of this example are summarized in Table 8.

Example 17

A 150 cc magnetic stirring type Hastelloy C autoclave was charged with methanol (32.0 g, 1.0 mole) with nitrogen pressure. The nitrogen overpressure was released and boron trifluoride (34.0 g, 0.5 mole) was added to the well stirred (2050 rpm), chilled methanol. Carbon monoxide was added to a pressure of 976 psi and the resulting reaction mixture was heated to 123° C.

To this autoclave was fed a 50/50 mixture of MTBE (29.1 g, 0.331 mole) and octane (29.1 g, 0.255 mole) over a period of 29 minutes at 123–124° C. and 1177–1270 psi. The pressure in the autoclave climbed to 1270 psi during the MTBE/octane introduction. Following the complete addition of the MTBE/octane, the reaction mixture was stirred at 125° C. for 30 minutes. The pressure in the autoclave slowly dropped to 1208 psi during this heating period.

The reaction mixture was cooled to 12° C., and the CO overpressure was released. The resulting reaction mixture (136.0 g) was added slowly to cooled, 5° C. to 15° C., methanol (143.9 g, 4.5 mole). The diluted reaction mixture reaction mixture was added to a 500 ml separatory funnel resulting in an upper octane phase and a lower acid product. The clear, light yellow octane phase (28.94 g) was analyzed by GC. GC analysis indicated methyl pivalate (1.58 g, 0.014 mole), nonanoic acid methyl esters (1.92 g, 0.01072 mole) and tridecanoic acid methyl esters (0.62 g, 0.0027 mole).

The volatile components were removed from the lower acid product phase (243.4 g) using a film evaporator operated at 15 mm and 50° C. The volatile components (158.9 g) were collected in a dry ice/methanol cooled receiving flask followed by two dry ice/methanol cooled traps. GC analysis of the volatile components by indicated methyl pivalate (10.74 g, 0.093 mole) and nonanoic acid methyl esters (1.5 g, 0.0084 mole).

The remaining clear, red liquid residual acid catalyst phase (79.53 g) was analyzed as predominately $BF_3.2CH_3OH$. The data of this example are summarized in Table 8.

Example 18

The procedures of Example 11 were repeated with the exceptions that no phosphoric acid was added. Methanol (38.4 g, 1.2 mole) and boron trifluoride (40.8 g, 0.6 mole) were added to the autoclave. MTBE (34.82 g, 0.396 mole) was added in over a time period of 16 minutes. GC analysis of the octane extracts revealed methyl pivalate (2.0 g, 0.0172 mole), nonanoic acid methyl esters (2.59 g, 0.0145 mole), and tridecanoic acid methyl esters (1.80 g, 0.0079 mole).

GC analysis of the volatile components recovered by film evaporation revealed methyl pivalate (6.80 g, 0.0586 mole), and nonanoic acid methyl esters (1.294 g, 0.00723 mole). The data of this example are summarized in Table 8.

Example 19

This Example demonstrates the ineffectiveness of $BF_3.2CH_3OH$ as an acid catalyst for the conversion of MTBE to methyl pivalate at 100° C. Procedures as described in Example 11 were followed. Methanol (40.0 g, 1.25 mole) was charged with nitrogen pressure to the autoclave. The nitrogen overpressure was released and the methanol cooled. BF$_3$ (42.5 g, 0.625 mole) was added to the stirred (1557 rpm) methanol over the course of 25 minutes at about a temperature of 20° C. to 40° C. The pressure in the autoclave was increased to 996 psi upon the addition of CO. The reaction mixture was heated to 95° C. and MTBE (20.63 g, 0.234 mole) was added over the course of 82 minutes at a temperature from about 95° C. to 100° C. and a pressure of about 1160–1311 psi. Following the complete addition of MTBE, the reaction mixture was stirred at 1311 psi for 30 minutes at about 100° C.

The reaction mixture was cooled to 17° C., and the CO overpressure was released. The resulting reaction mixture (126.5 g) was added to a 250 ml separatory funnel. The hazy colorless upper phase (8.90 g) was analyzed by GC. The GC analysis indicated only oligomers of isobutylene, mainly diisobutylene, triisobutylene and tetraisobutylene.

The clear deep orange lower acid phase (117.1 g) was added slowly to chilled methanol (117.1 g, 3.66 mole). The acid product was extracted three times with octane (3×30 ml). The combined octane extracts were analyzed by GC. GC analysis indicated diisobutylene, triisobutylene and tetraisobutylene with a trace amount of nonanoic acid methyl esters. The data of this example are summarized in Table 8.

collected octane phases revealed methyl pivalate (4.12 g, 0.0355 mole), nonanoic acid methyl esters (1.59 g, 0.0089 mole) and tridecanoic acid methyl esters (0.455 g, 0.002 mole). GC analysis of the collected volatile components from the acid product revealed methyl pivalate (6.99 g, 0.0603 mole) and nonanoic acid methyl esters (0.07 g, 0.00039 mole). The remaining acid product (188.43 g) was analyzed as BF$_3$2CH$_3$OH, which was of insufficient acid strength to convert MTBE to methyl pivalate at 25° C.

Example 21

In Example 21, highly branched nonenes were carbonylated with boron trifluoride dimethanol catalyst. The procedures were the same as Example 11 with exceptions. The exceptions were mainly during the product work-up. The decanoic acid methyl ester products were recovered by hexane extraction rather than octane extraction and no flash distillation was performed in this example.

The same apparatus was employed as Example 11. Into the autoclave was charged methanol (41.6 g, 1.3 mole) with nitrogen pressure. The nitrogen overpressure was released and boron trifluoride (44.2 g, 0.65 mole) with chilled water cooling and stirring (1254 rpm). To the contents of the autoclave was added carbon monoxide to 1086 psi. The reaction mixture was heated to 47° C., at 47° C. the carbon monoxide pressure was adjusted to 1208 psi. Highly branched nonenes (17.2 g, 0.1363 mole) were introduced

TABLE 8

| Example | BF$_3$ (moles) | MeOH | MIBF | T ° C. | P psi | H$_3$PO$_4$ | Octane Separation | Vacuum (mm, ° C.) | Products Selectivity MP | NA | TDA | Total Yield[b] % |
|---|---|---|---|---|---|---|---|---|---|---|---|---|
| 11 | 0.735 | 1.47 | 0.24 | 125 | 1210 | 0.184 | Yes | 1, 5 | 83 | 15 | 2 | 47 |
| 12 | note 1 | note 1 | .257 | 125 | 1250 | note 1 | Yes | 30, 90 | 48 | 35 | 17 | 40 |
| 13 | note 2 | note 2 | .257 | 123 | 1211 | note 2 | No | 30, 90 | 87 | 13 | — | 70 |
| 14 | note 3 | note 3 | .218 | 109 | 1220 | note 3 | No | 30, 90 | 46 | 32 | 15[a] | 31 |
| 15 | 0.735 | 1.47 | 0.24 | 125 | 1210 | — | Yes | 1, 50 | 87 | 12 | 1 | 49 |
| 16 | 0.735 | 1.47 | 0.24 | 150 | 1210 | — | Yes | 1, 50 | 97 | 3% | — | 44 |
| 17 | 0.5 | 1.0 | .331 | 125 | 1240 | — | Co-feed | 15, 50 | 83 | 15 | 2 | 39 |
| 18 | 0.6 | 1.2 | .396 | 125 | 1210 | — | Co-feed | 1, 50 | 77 | 14 | 9 | 71 |
| 19 | .625 | 1.25 | .234 | 100 | 1300 | — | — | — | — | trace | note 4 | — | note 1: The acid product was recycled from Example 11.
note 2: The acid product was recycled from Example 12.
note 3: The acid product was recycled from Example 13.
note 4: GC analysis indicated the presence of diisobutylene, triisobutylene, and tetraisobutylene
[a]Product also contained 7% of oligomer product
[b]Based on MTBE Example 20

This Example demonstrates the effectiveness of BF$_3$.CH$_3$OH as an acid catalyst for the carbonylation of MTBE to methyl pivalate at 25° C. This is the process practiced in the prior art. The Example also affirms the results of the prior art that BF$_3$.CH$_3$OH can not be recovered by distillation and thus be recycled in a process. The same procedures as Example 18 were employed with the exceptions that the following quantities of methanol (35.0 g, 1.094 mole) and BF$_3$ (74.4 g, 1.094 mole) were added. The MTBE (29.30 g, 0.333 mole) was added in 98 minutes. Prior to adding the reaction mixture to methanol, an attempt was made to distill acid catalyst from the reaction mixture. 6.5 g of acid catalyst was observed on distillation at atmospheric pressure at a temperature of 84° C. The remaining reaction mixture (135.1 g) was slowly added to cooled methanol (135.1 g, 4.22 mole). The same procedures for product recovery as Example 11 were used. GC analysis of the over the course of 1.5 minutes. The carbon monoxide pressure consumed during reaction was replenished and kept constant at 1200 psi. The reaction mixture was heated for an additional 120 minutes at 40–41° C. and 1200 psi carbon monoxide pressure. A significant drop in carbon monoxide was observed in the PVT during this heating period. The pressure in the autoclave was maintained at 1200 psi.

The reaction mixture was cooled to 15° C., at 15° C. the carbon monoxide overpressure was released. The contents (105.0 g) were removed from the autoclave and added to methanol (50 g, 1.56 mole). The resulting solution was extracted with hexane three times (10 ml each).

Gas chromatography analysis of the combined hexane phases revealed unreacted nonenes (8.5 g, 0.067 mole), decanoic acid methyl esters (19.14 g, 0.1029 mole), octadecenes (1.41 g, 0.0056 mole), and nonadecanoic acid methyl esters (2.7 g, 0.0086 mole).

Example 22

In Example 22, diisopropyl ether was converted to methyl isobutyrate. The acid catalyst was $BF_3 \cdot CH_3OH$ at 50° C. and 1200 psi. The procedure was similar to that of Example 18 with a few minor exceptions. Methanol (28.8 g, 0.9 mole) and $BF_3$ (61.2 g, 0.9 mole) were added to an autoclave. Also nonane was used to extract the products rather than octane. The diisopropyl ether (22.2 g, 0.22 mole) was added over a period of 52 minutes, and the reaction mixture was heated an additional 40 minutes following the addition of the ether.

The combined nonane extracts were analyzed by GC. The GC analysis indicated methyl isopropyl ether (0.3 g, 0.0035 mole), methyl-2-methyl propanoate or methyl isobutyrate (26.13 g, 0.256 mole). The volatiles (91.4 g) recovered by distillation on a rotary evaporator were also analyzed by GC. GC analysis indicated methyl isopropyl ether (0.071 g, 0.00082 mole), methyl-2-methyl propionate (6.53 g, 0.064 mole), and isopropyl isobutyrate (0.021 g, 0.00016 mole). The remaining acid catalyst (144.4 g) was predominantly $BF_3 \cdot 2CH_3OH$.

Having now fully described this invention, it will be appreciated by those skilled in the art that the invention can be performed within a wide range of parameters within what is claimed, without departing from the spirit and scope of the invention.

What is claimed is:

1. A method of making an ester comprising:
   (a) contacting an olefin selected from the group consisting of ethylene propylene, isoolefins, normal butenes, and $C_5$ to $C_{18}$ olefins with carbon monoxide and a $BF_3 2ROH$ acid composition to form a product composition;
   (b) adding ROH to the product composition of (a); and
   (c) separating a $BF_3 2ROH$ acid product from the ester, wherein ROH is selected from methanol; n-propanol; n-butanol; 2-propanol 2-ethyl hexanol; isohexanol; isoheptanol; isooctanol; isononanol; 3,5,5-trimethyl hexanol; isodecanol; isotridecanol; 1-octanol; 1-decanol; 1-dodecanol; 1-tetradecanol and mixtures thereof.

2. The method of claim 1 further comprising recycling a portion of the separated said product to contact the olefin.

3. The method of claim 1 wherein the olefin is an isoolefin.

4. The method of claim 2 wherein the olefin is isobutene.

5. The method of claim 1 wherein the olefin is contacted with carbon monoxide and a $BF_3 2ROH$ acid composition at a temperature fern about 60° C. to about 200° C.

6. The method of claim 5 wherein said temperature is from about 110° C. to about 160° C.

7. The method of claim 1 wherein the olefin is contacted with carbon monoxide and a $BF_3 2ROH$ acid composition at a pressure from about 30 atm to about 200 atm.

8. The method of claim 7 wherein said pressure is from about 110 atm to about 16 atm.

9. The method of claim 1 wherein ROH is methanol.

10. The method of claim 1 further comprising contacting the olefin with a saturated linear or bunched hydrocarbon having at least six carbons.

11. The method of claim 1 further comprising adding to the product composition a saturated linear or branched hydrocarbon having at least six carbons.

12. The method of claim 11 further comprising separating the hydrocarbon and ROH from $BF_3 2ROH$ and directing a of the separated hydrocarbon and the separated ROH to a unit selected horn the group consisting of a separation unit, a reaction unit, and a combination thereof.

13. The method of claim 1 further comprising contacting the olefin with phosphoric acid.

14. The method of claim 1 wherein the acid product is separated by concentrating the acid product such that the molar ratio $ROH:BF_3$ in the concentrated acid product is from about 2:1 to about 4:1.

15. The method of claim 14 wherein said molar ratio of $ROH:BF_3$ is from about 2:1 to about 3:1.

16. The method of claim 1 wherein the acid composition has a molar ratio of $ROH:BF_3$ from about 1.6:1 to about 3:1.

17. The method of claim 16 wherein said molar ratio is from about 1.9:1 to about 3:1.

18. The method of claim 1 wherein the product composition contains less than 3% by weight carboxylic acid.

19. A method of making methyl pivalate comprising:
   contacting methyl-t-butylether with carbon monoxide and a $BF_3 2CH_3OH$ acid composition to form a methyl pivalate product composition
   adding methanol to the product composition; and
   separating a $BF_3 2CH_3OH$ acid product from the methyl pivalate.

20. The method of claim 19 wherein the methyl-t-butylether is contacted with carbon monoxide and a $BF_3 2CH_3OH$ acid composition at a temperature of about 110° C. to about 160° C.

21. The method of claim 19 wherein the methyl-t-butylether is contacted with carbon monoxide and a $BF_3 2CH_3OH$ acid composition at a pressure from about 30 atm to about 200 atm.

22. The method of claim 19 further comprising contacting the methyl-t-butylether with a saturated linear or branched hydrocarbon having at least six carbons.

23. The method of claim 19 further comprising contacting the product composition with a saturated linear or branched hydrocarbon having at least six carbons.

24. The method of claim 23 further comprising separating the hydrocarbon and the methanol from the methyl pivalate and directing a portion of the separated hydrocarbon and the separated methanol to a unit selected from the group consisting of a separation unit, a reaction unit, and a combination thereof.

25. The method of clam 19 further comprising contacting the methyl-t-butylether with phosphoric acid.

26. The method of claim 19 wherein the acid product is separated by concentrating the acid product such that the molar ratio $ROH:BF_3$ in the acid product is from about 2:1 to about 4:1.

27. The method of claim 26 wherein said molar ratio of $ROH:BF_3$ is from about 2:1 to about 3:1.

28. The method of claim 19 wherein the acid composition has a molar ratio of $ROH:BF_3$ from about 1.6:1 to about 3:1.

29. The method of claim 28 wherein said molar ratio is from about 1.9:1 to about 3:1.

30. The method of claim 19 wherein the product composition contains nonanoic methyl esters such that the molar ratio of methyl pivalate to nonanoic methyl esters is about 4 or greater.

31. A method of making an ester comprising:
   (a) contacting an olefin selected from the group consisting of ethylene, propylene, isoolefins, normal butenes, and $C_5$ to $C_{18}$ olefins with carbon monoxide and a $BF_3$, ROH acid composition to form a product composition;
   (b) adding ROH to the product composition of (a); and
   (c) separating a $BF_3 ROH$ maid product from the ester, wherein ROH is selected from methanol; n-propanol;

2-propanol; u-butanol 2-ethyl hexanol; isohexanol; isoheptanol; isooctanol; isononanol; 3,5,5-trimethyl hexanol; isodecanol; isotridecanol; 1-octanol; 1-decanol; 1-dodecanol; 1-tetradecanol mid mixtures thereof and wherein the molar equivalents of ROH in the $BF_3ROH$, ranges from about 2 to about 4.

32. A method of making an ester comprising:

(a) contacting an ether with carbon monoxide and a $BF_3 2ROH$ acid composition to form a product composition;

(b) adding ROH to the product composition of (a); and (c) separating a $BF_3 2ROH$ acid product from the ester, wherein ROH is selected from methanol; n-propanol; n-butanol; 2-propanol 2-ethyl hexanol; isohexanol; isoheptanol; isooctanol; isononanol; 3,5, 5-trimethyl hexanol; isodecanol; isotridecanol 1-octanol; 1-decanol; 1-dodecanol; 1-tetradecanol and mixtures thereof.

33. The method of claim 32 further comprising recycling a portion of the separated acid product to contact the ether.

34. The method of claim 32 wherein the other is represented by the formula R'—O—R", wherein R'= saturated $C_1$–$C_{13}$ alkyl and R"=saturated $C_1$–$C_{13}$ alkyl, and R' and R" can be the same or different.

35. The method of claim 32 wherein the ether is methyl-t-butylether.

36. The method of claim 32 wherein the ether is contacted with carbon monoxide and a $BF_3 2ROH$ acid composition at a temperature from about 60° C. to about 200° C.

37. The method of claim 36 wherein said temperature is from about 110° C. to about 160° C.

38. The method of claim 32 wherein the ether is contacted with carbon monoxide and a $BF_3 2OH$ acid composition at a pressure from about 30 atm to about 200 atm.

39. The method of claim 38 wherein said pressure is from about 110 atm to about 160 atm.

40. The method of claim 32 wherein ROH is methanol.

41. The method of claim 32 wherein the ether is methyl-t-butyl ether.

42. The method of claim 32 wherein the ether is diisopropyl ether and ROH is 2-propanol.

43. The method of claim 32 further comprising contacting the ether with a saturated linear or branched hydrocarbon having at least six carbons.

44. The method of claim 32 further comprising adding to the product composition a saturated linear or branched hydrocarbon having at least six carbons.

45. The method of claim 44 further comprising separating the hydrocarbon and ROH from $BF_3 2ROH$ and directing a portion of the separated hydrocarbon and the separated ROH to a unit selected from the group consisting of separation unit, a reaction unit, and a combination thereof.

46. The method of claim 32 further comprising contacting the ether with phosphoric acid.

47. The method of claim 32 wherein die acid product is separated by concentrating the acid product such that the molar ratio $ROH:BF_3$ in the concentrated acid product is from about 2:1 to about 4:1.

48. The method of claim 47 wherein said molar ratio of $ROH:BF_3$ is about 2:1 to about 3:1.

49. The method of claim 32 wherein the acid composition has a molar ratio of $ROH:BF_3$ from about 1.6:1 to about 3:1.

50. The method of claim 49 wherein said molar ratio of $ROH:BF_3$ is from about 1.9:1 to about 3:1.

51. The method of claim 32 wherein the product composition contains less than 3% by weight carboxylic acid.

52. A method of making an ester comprising:

(a) contacting an ether with carbon monoxide and a $BF_3$ ROH acid composition to form a product composition;

(b) adding ROH to the product composition of (a); and (c) separating a $BF_3ROH$ acid product from the ester, wherein ROH is selected from methanol; n-propanol; n-butanol; 2-butanol 2-ethyl hexanol; isohexanol; isoheptanol; isooctanol; isononanol; 3,5,5-trimethyl hexanol; isodecanol; isotridecanol; 1-octanol; 1-decanol; 1-dodecanol; 1-tetradecanol and mixtures thereof and wherein the molar equivalents of ROH in the $BF_3ROH$, ranges from about 2 to about 4.

* * * * *